US009089507B2

(12) United States Patent
Moeck et al.

(10) Patent No.: US 9,089,507 B2
(45) Date of Patent: Jul. 28, 2015

(54) USE OF ORITAVANCIN FOR PREVENTION AND TREATMENT OF ANTHRAX

(75) Inventors: Gregory Moeck, St. Laurent (CA); Thomas Reeves Parr, Jr., Indianapolis, IN (US)

(73) Assignee: THE MEDICINES COMPANY, Parsippany, NJ (US)

( * ) Notice: Subject to any disclaimer, the term of this patent is extended or adjusted under 35 U.S.C. 154(b) by 636 days.

(21) Appl. No.: 12/442,751

(22) PCT Filed: Sep. 24, 2007

(86) PCT No.: PCT/US2007/079277

§ 371 (c)(1), (2), (4) Date: Mar. 25, 2009

(87) PCT Pub. No.: WO2008/097364

PCT Pub. Date: Aug. 14, 2008

(65) Prior Publication Data

US 2010/0041585 A1 Feb. 18, 2010

Related U.S. Application Data

(60) Provisional application No. 60/847,397, filed on Sep. 25, 2006.

(51) Int. Cl.

*A61K 38/14* (2006.01)
*A61K 31/00* (2006.01)
*A61K 31/7052* (2006.01)

(52) U.S. Cl.

CPC ............. *A61K 31/00* (2013.01); *A61K 31/7052* (2013.01); *A61K 38/14* (2013.01)

(58) Field of Classification Search

CPC ...................................................... A61K 38/14

See application file for complete search history.

(56) References Cited

U.S. PATENT DOCUMENTS

2003/0176327 A1* 9/2003 Cassell et al. ..................... 514/8
2005/0277581 A1 12/2005 Stogniew

OTHER PUBLICATIONS

Vippagunta "Crystalline solids," Adv. Drug Delivery Rev., 2001, 48, 3-26.*

Byrn et al. Solid State Chemistry of Drugs, 2 Ed. 1999 "Hydrates and Solvates" pp. 233-247.*

Brook "The prophylaxis and treatment of anthrax," International Journal of Antimicrobial Agents 20 (2002) 320-325.*

Fetterly et al. "Pharmacokinetics of Oritavancin in Plasma and Skin Blister Fluid following Administration of a 200-Milligram Dose for 3 Days or a Single 800-Milligram Dose," Antimicrobial Agents and Chemotherapy, Jan. 2005, vol. 49, No. 1, p. 148-152.*

Boylan et al. "Pharmacodynamics of Oritavancin (LY333328) in a Neutropenic-Mouse Thigh Model of *Staphylococcus aureus* Infection," Antimicrobial Agents and Chemotherapy, May 2003, vol. 47, No. 5, p. 1700-1706.*

Dorr et al. "Human pharmacokinetics and rationale for once-weekly dosing of dalbavancin, a semi-synthetic glycopeptide" Journal of Antimicrobial Chemotherapy (2005) 55, Suppl. S2, ii25-ii30.*

Field Manual "Treatment of Biological Warfare Agent Casualties" Headquarters, Departments of the Army, the Navy and the Air Force, and Commandant, Marine Corps, Jul. 17, 2000, pp. 2-1-2-4.*

Turnball et al. "MICS of Selected Antibiotics for *Bacillus anthracis, Bacillus cereus, Bacillus thuringiensis*, and *Bacillus mycoides* from a Range of Clinical and Environmental Sources as Determined by the Ernst," Journal of Clinical Microbiology, Aug. 2004, vol. 42, No. 8, p. 3626-3634).*

Dixon et al. "Early *Bacillus anthracis*—macrophage interactions: intracellular survival and escape," Cellular Microbiology 2000, vol. 2. No. 6, p. 453-463.*

Easmon et al. "Uptake of ciprofloxacin by macrophages" Journal of Clinical Pathology 1985 vol. 38, p. 442-444.*

"Use of Anthrax Vaccine in the United States: Recommendations of the Advisory Committee on Immunization Practices (ACIP), 2009" Recommendations and Reports Jul. 23, 2010, 59(RR06), 1-30.*

Susman, E., ICAAC Dalbavancin Tested as Treatment for Exposure to Anthrax, Dec. 20, 2005, Doctor's Guide, Global Edition, website (http://www.pslgroup.comidg/2560E6.htm), cited in European Official Action, EU Appln. No. 07 872 765.8, dated Sep. 4, 2009.

Heine HS, Bassett J, Miller L. In vitro and in vivo activity of dalbavancin (DAL) against *Bacillus anthracis* (BA) [abstr]. In: Proceedings of the 45th Interscience Conference on Antimicrobial Agents and Chemotherapy. Washington, DC, Dec. 16-19, 2005. American Society of Microbiology, 2005. Abstract F-2079; p. 232.

Ward et al, Oritavancin—An Investigational Glycopeptide Antibiotic, Expert Opinion on Investigational Drugs, Apr. 2006, vol. 15, No. 4, pp. 417-429.

Sejvar et al, Management of Anthrax Meningitis, Lancet Infectious Diseases, vol. 5, No. 5, May 2005, pp. 287-295.

Jernigan et al, Bioterrorism-Related Inhalational Anthrax: The First 10 Cases Reported in the United States, Emerging Infectious Diseases, vol. 7, No. 6, 2001, pp. 933-944.

Boylan et al, Pharmacodynamics of Oritavancin (LY333328) in a Neutropenic-Mouse Thigh Model of *Staphylococcus aureus* Infection, Antimicrobial Agents and Chemotherapy, vol. 47, No. 5, May 2003, pp. 1700-1706.

Heine et al. 2001. In Vitro Activity of Oritavancin (LY333328), Levofloxacin, Meropenem, GAR936 and Linezolid against Strains of *Bacillus anthracis*. Interscience Conference on Antimicrobial Agents and Chemotherapy (41st : 2001 : Chicago, Ill.). Abstr Intersci Conf Antimicrob Agents Chemother Intersci Conf Antimicrob Agents Chemother. Dec. 16-19, 2001; 41: abstract No. E-524.

International Search Report and Written Opinion for PCT/US2007/079277.

* cited by examiner

*Primary Examiner* — Christina Bradley

(74) *Attorney, Agent, or Firm* — Roylance, Abrams, Berdo & Goodman, L.L.P.

(57) ABSTRACT

Glycopeptide antibiotics, such as oritavancin, demonstrate significant activity against *B. anthracis*. Methods for the treatment, prophylaxis and prevention of *B. anthracis* infection and disease in animals, including humans, are described.

16 Claims, 9 Drawing Sheets

USE OF ORITAVANCIN FOR PREVENTION AND TREATMENT OF ANTHRAX

BACKGROUND OF THE INVENTION

The causative agent of anthrax is *Bacillus anthracis*, a Gram-positive spore-forming rod-shaped bacterium. The Center for Disease Control and Prevention recognizes this bacterium as a Category A agent with recognized bioterrorism potential (bt.cdc.gov/agent/anthrax/needtoknow.asp; Sep. 21, 2006).

Anthrax is a serious disease and can be contracted by cutaneous exposure, ingestion, or inhalation, leading to cutaneous, gastrointestinal and inhalational disease, respectively. Cutaneous anthrax occurs when spores gain access through a cut or abrasion in the skin. The organisms germinate and produce toxins that result in a local reaction with swelling and eschar formation. The disease may progress to bacteremia, and mortality is reported in up to 20 percent of untreated cutaneous cases. Cutaneous anthrax can be recognized clinically, and morbidity and mortality are low with appropriate antimicrobial therapy. Gastrointestinal disease is usually associated with the ingestion of anthrax-contaminated meat. Gastrointestinal disease can be prevented through the effective inspection of livestock and meat products entering the marketplace. Inhalational anthrax follows aerosolized exposure to the spores of *B. anthracis* with subsequent germination of the spores, toxin production, and invasion of the tissues and blood stream by the organism. After a usual incubation period of 2 to 6 days, exposed individuals develop symptomatic disease with very high mortality.

Of the routes of exposure, inhalation anthrax poses the highest mortality rate at approximately 40-80% (Jernigan et al. *Emerg Infect Dis.* 2001. 7(6):933-944; Meselson et al. *Science* 1994. 266:1202-1208). As such, inhalation of anthrax spores it is the most likely exposure route to be exploited in warfare or during a terrorist attack.

Three types of antibiotics are approved for anthrax: a fluoroquinolone (ciprofloxacin), tetracyclines (including doxycycline), and β-lactams (penicillin). These chemotherapies are most effective when given immediately following exposure to *B. anthracis* spores; longer delays before initiation of therapy is correlated with worsened outcome. For inhalation anthrax, patients are typically prescribed one or two additional antibiotics, which might include rifampin, vancomycin, penicillin, ampicillin, chloramphenicol, imipenem, clindamycin, or clarithromycin. Initial treatment is by vein (intravenous, or IV), followed by medication by mouth. A course of ciprofloxacin therapy lasting 60 days is the current standard of care for anthrax post-exposure prophylaxis. Other studies recommend even longer courses of antibiotic therapy, at least four months in duration, to reduce the risk of mortality following exposure to significant levels of the organism (Brookmeyer et al. *Proc Natl Acad Sci USA.* 2003. 100: 10129-10132). These long durations of therapy are associated with patient non-compliance and failure to receive the entire prescribed dose (Brookmeyer et al., ib.). The pharmacokinetics of these antibacterial agents typically impose twice-daily (or even more frequent) dosing to maintain drug at adequate (protective) levels. Fatalities have occurred despite the administration of antibiotics to patients exposed to *B. anthracis* bacteria (Jernigan et al., ib.).

The possibility of emerging natural resistance or "engineered" resistance in *B. anthracis* is also an area of great concern (Inglesby et al. 2002. *J. Am. Med. Assoc.* 287:2236-2252). For example, although penicillin has long been considered the treatment of choice for anthrax, numerous reports of β-lactamase-producing strains, and treatment failures have appeared in the literature (Bradaric and Punda-Polic 1992. *Lancet* 340:306-307; Doganay and Aydin, 1991. *Scand J Infect Dis.* 23:333-335; Gold 1955. *Arch. Intern. Med.* 96:387-396; Lightfoot et al. 1990. *Salisbury Med. Bull.* 68 (Suppl): 95-98). Additionally, two open reading frames coding for β-lactamases have been identified in the *B. anthracis* genome (Chen et al. 2004. *Antimicrob. Agents Chemother.* 48:4873-4877; Materon et al. 2003. *Antimicrob. Agents Chemother.* 47:2040-2042). More recently, several reports of *B. anthracis* resistance to ciprofloxacin, macrolides, and tetracyclines have appeared in the literature (Brook et al. 2001. *Int. J. Antimicrob. Agents* 18:559-562; Choe et al. 2000. *Antimicrob. Agents Chemother.* 44:1766; Price et al. 2003. *Antimicrob. Agents Chemother.* 47:2362-2365). With the added concern of engineered resistance in a biological threat setting (Leitenberg, 1993. *Biologicals* 212:187-191; Pile et al. 1998. *Arch. Itern. Med.* 158:429-434), it becomes important to assess the spectrum of antibiotics available for treatment.

The current inhalation anthrax animal model for antibiotic testing utilizes rhesus monkeys that are both expensive and in short supply (Friedlander et al. 1993. *J. Inf. Dis.* 167:1239-1242). The use of a small rodent model both decreases the cost per antibiotic test and increases the number of animals per test group as well as the number of antibiotics that can be tested at any given time. The application of pre-determined dose and schedule based on "murine" infection modeling has been shown to greatly expand the utility of these small animal models and allow testing of "humanized" dosing for success or failure prior to the more expensive and difficult non-human primate models (Deziel et al. 2005. *Antimicrob. Agents Chemother.* 49:5099-5106).

The current standard of care for treatment of anthrax is thus lengthy, inconvenient, and not entirely effective, and alternative compounds for use in the treatment, as well as prophylaxis and prevention, of anthrax are needed. In particular, alternative compounds for use in the treatment, prophylaxis and prevention of inhalation anthrax are needed.

SUMMARY OF THE INVENTION

As disclosed herein, it has been discovered that the glycopeptide antibiotic oritavancin, also known in the art and referred to herein as $N^{DISACC}$-(4-(4-chlorophenyl)benzyl) A82846B and LY333328, demonstrates significant activity, both in vitro and in vivo, against the vegetative form of *B. anthracis* and against *B. anthracis* spores. The results of the experiments described herein demonstrate that glycopeptide antibiotics, such as oritavancin (or a pharmaceutically acceptable salt, hydrate, or solvate thereof, or a mixture thereof), will be efficacious in the treatment, prophylaxis and/or prevention of infection and disease caused by *B. anthracis* in animals, including humans.

Inhibiting *B. anthracis*

The invention includes methods of inhibiting *B. anthracis* bacteria, in vitro, in vivo and/or ex vivo, comprising contacting *B. anthracis* with a glycopeptide antibiotic in an amount sufficient to inhibit *B. anthracis* bacteria. *B. anthracis* may be in the form of a vegetative cell, a spore or a mixture of both. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention further includes methods of inhibiting the growth of *B. anthracis* bacteria, in vitro, in vivo and/or ex vivo, comprising contacting *B. anthracis* with a glycopeptide antibiotic in an amount sufficient to inhibit the growth of *B. anthracis* bacteria. *B. anthracis* may be in the form of a vegetative cell, a spore or a mixture of both. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is also directed to a method of inhibiting activation of a *B. anthracis* spore, in vitro, in vivo and/or ex vivo, comprising contacting a *B. anthracis* spore with a glycopeptide antibiotic in an amount sufficient to inhibit activation of a *B. anthracis* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is further directed to a method of inhibiting germination of a *B. anthracis* spore, in vitro, in vivo and/or ex vivo, comprising contacting a *B. anthracis* spore with a glycopeptide antibiotic in an amount sufficient to inhibit germination of a *B. anthracis* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is additionally directed to a method of inhibiting outgrowth of a *B. anthracis* spore, in vitro, in vivo and/or ex vivo, comprising contacting a *B. anthracis* spore with a glycopeptide antibiotic in an amount sufficient to inhibit outgrowth of a *B. anthracis* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Moreover, the invention is directed to a method of inhibiting growth of a vegetative form of *B. anthracis*, in vitro, in vivo and/or ex vivo, comprising contacting a vegetative form of *B. anthracis* with a glycopeptide antibiotic in an amount sufficient to inhibit a vegetative form of *B. anthracis*. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Treatment of *B. anthracis* Infections

The invention is generally directed to methods of treating a *B. anthracis* infection in a subject, comprising administering a therapeutically effective amount of a glycopeptide antibiotic to a subject having a *B. anthracis* infection. *B. anthracis* may be in the form of a vegetative cell, a spore, or a mixture of both. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

The invention is also directed to a method of treating a *B. anthracis* infection in a subject, comprising administering a therapeutically effective amount of a glycopeptide antibiotic to a subject having a *B. anthracis* infection, wherein said treatment inhibits activation of a *B. anthracis* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

The invention is further directed to a method of treating a *B. anthracis* infection in a subject, comprising administering a therapeutically effective amount of a glycopeptide antibiotic to a subject having a *B. anthracis* infection, wherein said treatment inhibits germination of a *B. anthracis* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

The invention is additionally directed to a method of treating a *B. anthracis* infection in a subject, comprising administering a therapeutically effective amount of a glycopeptide antibiotic to a subject having a *B. anthracis* infection, wherein said treatment inhibits outgrowth of a *B. anthracis* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

Moreover, the invention is directed to a method of treating a *B. anthracis* infection in a subject, comprising administering a therapeutically effective amount of a glycopeptide antibiotic to a subject having a *B. anthracis* infection, wherein said treatment inhibits growth of a vegetative form of *B. anthracis*. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

Prevention of *B. anthracis* Infections

The invention is also directed to a method of preventing a *B. anthracis* infection in a subject, comprising administering to a subject at risk of exposure to *B. anthracis* an amount of a glycopeptide antibiotic sufficient to prevent *B. anthracis* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject less than 48 hours, less than 36 hours, less than 24 hours, less than 12 hours or less than 6 hours before risk of exposure to *B. anthracis*. The exposure to *B. anthracis* infection may be a cutaneous exposure, exposure by ingestion, or exposure by inhalation. The duration of prevention of infection may be at least 15 days, 30 days, 45 days or 60 days. Preferably, the subject has not previously been exposed to *B. anthracis*.

The invention is also directed to a method for inhibiting colonization of a subject by *B. anthracis*, comprising administering to a subject at risk of exposure to *B. anthracis* an amount of a glycopeptide antibiotic sufficient to inhibit colonization of a subject by *B. anthracis*. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject less than 48 hours, less than 36 hours, less than 24 hours, less than 12 hours or less than 6 hours before risk of exposure to *B. anthracis*. The exposure to *B. anthracis* infection may be a cutaneous exposure, exposure by ingestion, or exposure by inhalation. The duration of prevention of infection may be at least 15 days, 30 days, 45 days or 60 days. Preferably, the subject has not previously been exposed to *B. anthracis*.

Prophylaxis of *B. anthracis* Infection

The invention is further generally directed to methods for providing prophylaxis of a *B. anthracis* infection in a subject, comprising administering to a subject having a *B. anthracis* infection an amount of a glycopeptide antibiotic sufficient to achieve prophylaxis of a *B. anthracis* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection. Preferably, the prophylaxis is an asymptomatic infection in said subject.

The present invention also includes the use of a glycopeptide antibiotic in the manufacture of a medicament for the treatment of *B. anthracis* infection in a subject. Preferably, said glycopeptide antibiotic is oritavancin, or pharmaceutically acceptable salt, hydrate, or solvate thereof, or a mixture thereof.

The present invention further includes the use of a glycopeptide antibiotic in the manufacture of a medicament for the prophylaxis of *B. anthracis* infection in a subject. Preferably, said glycopeptide antibiotic is oritavancin, or pharmaceutically acceptable salt, hydrate, or solvate thereof, or a mixture thereof.

The present invention additionally includes the use of a glycopeptide antibiotic in the manufacture of a medicament for the prevention of *B. anthracis* infection in a subject. Preferably, said glycopeptide antibiotic is oritavancin, or pharmaceutically acceptable salt, hydrate, or solvate thereof, or a mixture thereof.

Moreover, the invention includes a kit comprising the pharmaceutical composition or a glycopeptide antibiotic of the present invention and written instructions.

DETAILED DESCRIPTION OF THE INVENTION

Figure 1:
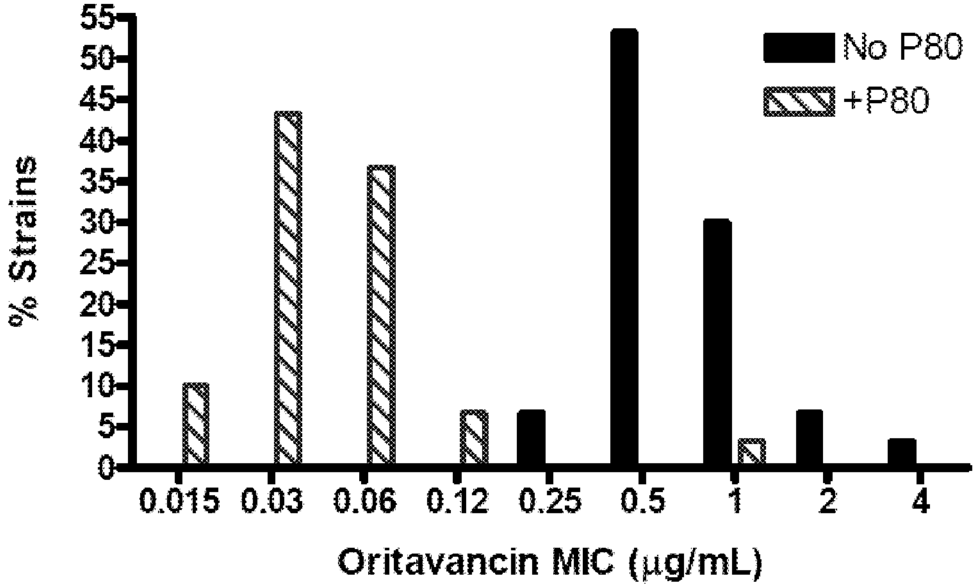
FIG. 1 depicts oritavancin susceptibility distributions for *B. anthracis* (n=30) in the absence and presence of polysorbate-80. Susceptibilities were determined by broth microdilution according to CLSI guidelines with 30 strains of *B. anthracis* in the presence and absence of 0.002% polysorbate-80. Abbreviations: "No P80", no polysorbate-80; "+P80", with 0.002% polysorbate-80.

Applicants have discovered that oritavancin can be used in the treatment of *B. anthracis* infection in mammals. As such, the present invention provides methods for the inhibition of *B. anthracis* and methods for the treatment of *B. anthracis* infection in a subject, such as a mammal, preferably a human.

Inhibiting *B. anthracis*

The invention includes methods of inhibiting *B. anthracis* bacteria, in vitro, in vivo and/or ex vivo, comprising contacting *B. anthracis* with a glycopeptide antibiotic in an amount sufficient to inhibit *B. anthracis* bacteria. *B. anthracis* may be in the form of a vegetative cell, a spore or a mixture of both. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention further includes methods of inhibiting the growth of *B. anthracis* bacteria, in vitro, in vivo and/or ex vivo, comprising contacting *B. anthracis* with a glycopeptide antibiotic in an amount sufficient to inhibit the growth of *B. anthracis* bacteria. *B. anthracis* may be in the form of a vegetative cell, a spore or a mixture of both. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is also directed to a method of inhibiting activation of a *B. anthracis* spore, in vitro, in vivo and/or ex vivo, comprising contacting a *B. anthracis* spore with a glycopeptide antibiotic in an amount sufficient to inhibit activation of a *B. anthracis* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is further directed to a method of inhibiting germination of a *B. anthracis* spore, in vitro, in vivo and/or ex vivo, comprising contacting a *B. anthracis* spore with a glycopeptide antibiotic in an amount sufficient to inhibit germination of a *B. anthracis* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

The invention is additionally directed to a method of inhibiting outgrowth of a *B. anthracis* spore, in vitro, in vivo and/or ex vivo, comprising contacting a *B. anthracis* spore with a glycopeptide antibiotic in an amount sufficient to inhibit outgrowth of a *B. anthracis* spore. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Moreover, the invention is directed to a method of inhibiting growth of a vegetative form of *B. anthracis*, in vitro, in vivo and/or ex vivo, comprising contacting a vegetative form of *B. anthracis* with a glycopeptide antibiotic in an amount sufficient to inhibit a vegetative form of *B. anthracis*. The glycopeptide antibiotic may be in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

Treatment of *B. anthracis* Infections

The invention is generally directed to methods of treating a *B. anthracis* infection in a subject, comprising administering a therapeutically effective amount of a glycopeptide antibiotic to a subject having a *B. anthracis* infection. *B. anthracis* may be in the form of a vegetative cell, a spore, or a mixture of both. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

The invention is also directed to a method of treating a *B. anthracis* infection in a subject, comprising administering a therapeutically effective amount of a glycopeptide antibiotic to a subject having a *B. anthracis* infection, wherein said treatment inhibits activation of a *B. anthracis* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

The invention is further directed to a method of treating a *B. anthracis* infection in a subject, comprising administering a therapeutically effective amount of a glycopeptide antibiotic to a subject having a *B. anthracis* infection, wherein said treatment inhibits germination of a *B. anthracis* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

The invention is additionally directed to a method of treating a *B. anthracis* infection in a subject, comprising administering a therapeutically effective amount of a glycopeptide antibiotic to a subject having a *B. anthracis* infection, wherein said treatment inhibits outgrowth of a *B. anthracis* spore. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

Moreover, the invention is directed to a method of treating a *B. anthracis* infection in a subject, comprising administering a therapeutically effective amount of a glycopeptide antibiotic to a subject having a *B. anthracis* infection, wherein said treatment inhibits growth of a vegetative form of *B. anthracis*. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection.

Prevention of *B. anthracis* Infections

The invention is also directed to a method of preventing a *B. anthracis* infection in a subject, comprising administering to a subject at risk of exposure to *B. anthracis* an amount of a glycopeptide antibiotic sufficient to prevent *B. anthracis* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject less than 48 hours, less than 36 hours, less than 24 hours, less than 12 hours or less than 6 hours before risk of exposure to *B. anthracis*. The exposure to *B. anthracis* infection may be a cutaneous exposure, exposure by ingestion, or exposure by inhalation. The duration of prevention of infection may be at least 15 days, 30 days, 45 days or 60 days. Preferably, the subject has not previously been exposed to *B. anthracis*.

The invention is also directed to a method for inhibiting colonization of a subject by *B. anthracis*, comprising administering to a subject at risk of exposure to *B. anthracis* an amount of a glycopeptide antibiotic sufficient to inhibit colonization of a subject by *B. anthracis*. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject less than 48 hours, less than 36 hours, less than 24 hours, less than 12 hours or less than 6 hours before risk of exposure to *B. anthracis*. The exposure to *B. anthracis* infection may be a cutaneous exposure, exposure by ingestion, or exposure by inhalation. The duration of prevention of infection may be at least 15 days, 30 days, 45 days or 60 days. Preferably, the subject has not previously been exposed to *B. anthracis*.

Prophylaxis of *B. anthracis* Infection

The invention is further generally directed to methods for providing prophylaxis of a *B. anthracis* infection in a subject, comprising administering to a subject having a *B. anthracis* infection an amount of a glycopeptide antibiotic sufficient to achieve prophylaxis of a *B. anthracis* infection. Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof. Preferably, the glycopeptide antibiotic is administered to the subject within 48 hours of infection, within 36 hours of infection, within 24 hours of infection, within 12 hours of infection or within 6 hours of infection. Preferably, the prophylaxis is an asymptomatic infection in said subject.

The present invention also includes the use of a glycopeptide antibiotic in the manufacture of a medicament for the treatment of *B. anthracis* infection in a subject. Preferably, said glycopeptide antibiotic is oritavancin, or pharmaceutically acceptable salt, hydrate, or solvate thereof, or a mixture thereof.

The present invention further includes the use of a glycopeptide antibiotic in the manufacture of a medicament for the prophylaxis of *B. anthracis* infection in a subject. Preferably, said glycopeptide antibiotic is oritavancin, or pharmaceutically acceptable salt, hydrate, or solvate thereof, or a mixture thereof.

The present invention additionally includes the use of a glycopeptide antibiotic in the manufacture of a medicament for the prevention of *B. anthracis* infection in a subject. Preferably, said glycopeptide antibiotic is oritavancin, or pharmaceutically acceptable salt, hydrate, or solvate thereof, or a mixture thereof.

Moreover, the invention includes a kit comprising the pharmaceutical composition or a glycopeptide antibiotic of the present invention and written instructions.

The glycopeptide antibiotics of the present invention include those of Formula I:

Formula I

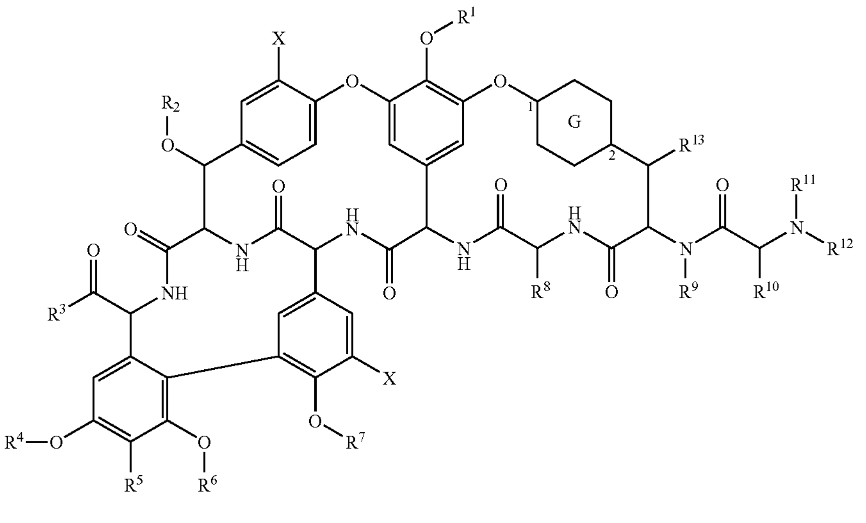

as well as pharmaceutically acceptable salts, hydrates and solvates thereof, and mixtures thereof, wherein:

$R^1$ is one of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$; or $R^1$ is a saccharide group optionally substituted with —$R^a$—Y—$R^b$—$(Z)_x$, $R^f$, —C(O)$R^f$, or —C(O)—$R^a$—Y—$R^b$—$(Z)_x$;

$R^2$ is hydrogen or a saccharide group optionally substituted with —$R^a$—Y—$R^b$—$(Z)_x$, $R^f$, —C(O)$R^f$, or —C(O)—$R^a$—Y—$R^b$—$(Z)_x$;

$R^3$ is —$OR^c$, —$NR^cR^c$, —O—$R^a$—Y—$R^b$—$(Z)_x$, —$NR^c$—$R^a$—Y—$R^b$—$(Z)_x$, —$NR^cR^e$ or —O—$R^e$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$(Z)_x$, $R^f$, or —C(O)—$R^a$—Y—$R^b$—$(Z)_x$, or $R^4$ and $R^5$ can be joined, together with the atoms to which they are attached, to form a heterocyclic ring optionally substituted with —$NR^c$—$R^a$—Y—$R^b$—$(Z)_x$;

$R^5$ is selected from the group consisting of hydrogen, halo, —CH($R^c$)—$NR^cR^c$, —CH($R^c$)—$NR^cR^e$, —CH($R^c$)—$NR^c$—$R^a$—Y—$R^b$—$(Z)_x$, —CH($R^c$)—$R^x$, and —CH($R^c$)—$NR^c$—$R^a$—C(O)—$R^x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, $R^f$, —C(O)$R^f$, or —C(O)—$R^a$—Y—$R^b$—$(Z)_x$, or $R^5$ and $R^6$ can be joined, together with the atoms to which they are attached, to form a heterocyclic ring optionally substituted with —$NR^c$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$, and —C(O)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)$R^d$, —C(NH)$R^d$, —C(O)$NR^cR^c$, —C(O)$OR^d$, —C(NH)$NR^cR^c$, —$R^a$—Y—$R^b$—$(Z)_x$, and —C(O)—$R^b$—Y—$R^b$—$(Z)_x$, or $R^{11}$ and $R^{12}$ are joined, together with the nitrogen atom to which they are attached, to form a heterocyclic ring;

$R^{13}$ is selected from the group consisting of hydrogen or —$OR^{14}$;

$R^{14}$ is selected from hydrogen, —C(O)$R^d$ and a saccharide group;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is each a saccharide group;

$R^f$ is each independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;

$R^x$ is an N-linked amino saccharide or an N-linked heterocycle;

X is each independently selected from hydrogen, fluoro, chloro, bromo or iodo;

Y is each independently selected from the group consisting of, —$CH_2$—, oxygen, sulfur, —S—S—, —$NR^c$—, —S(O)—, —$SO_2$—, —$NR^c$C(O)—, —$OSO_2$—, —OC(O)—, —N($R^c$C)$SO_2$—, —C(O)$NR^c$—, —C(O)O—, —$SO_2NR^c$—, —$SO_2$O—, —P(O)($OR^c$)O—, —P(O)($OR^c$)$NR^c$—, —OP(O)($OR^c$)O—, —OP(O)($OR^c$)$NR^c$—, —OC(O)O—, —$NR^c$C(O)O—, —$NR^c$C(O)$NR^c$—, —OC(O)$NR^c$—, —C(O)—, and —N($R^c$)$SO_2NR^c$—;

Z is each independently selected from hydrogen, aryl, cycloalkyl, cycloalkenyl, heteroaryl, heterocyclic; or a saccharide.

x is 1 or 2; and

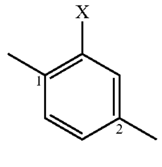

or

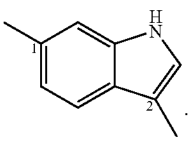

is selected from

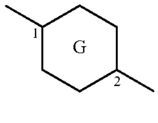

In particular, the glycopeptide antibiotics of Formula I include oritavancin, teicoplanin, dalbavancin and telavancin.

The glycopeptide antibiotics of the present invention also include those of Formula II:

Formula II

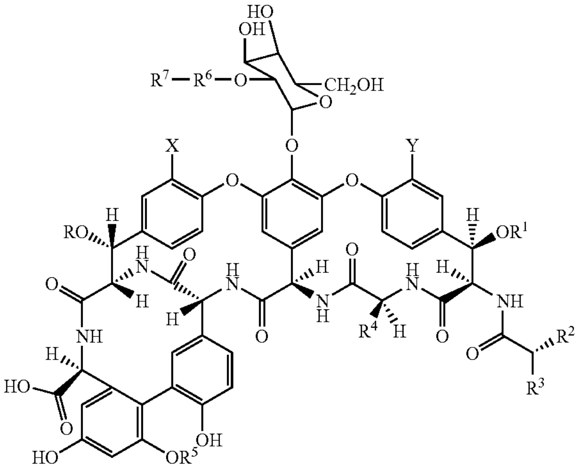

as well as pharmaceutically acceptable salts, hydrates and solvates thereof, and mixtures thereof, wherein:

X and Y are each independently hydrogen or chloro;

R is hydrogen, 4-epi-vancosaminyl, actinosaminyl, ristosaminyl, or a group of the formula —$R^a$—$R^{7a}$, wherein $R^a$ is 4-epi-vancosaminyl, actinosaminyl, or ristosaminyl, and $R^{7a}$, defined below, is attached to the amino group of $R^a$;

$R^1$ is hydrogen or mannose;

$R^2$ is —$NH_2$, —$NHCH_3$, —$N(CH_3)_2$, —$NHR^{7b}$, or —$N(CH_3)R^{7b}$, wherein $R^{7b}$ is defined below;

$R^3$ is —$CH_2CH(CH_3)_2$, [p-OH, m-Cl]phenyl, p-rhamnosyloxyphenyl, p-(rhamnosyl-galactosyloxy)-phenyl, [p-galactose-galactose]phenyl, p-(methoxyrhamnosyloxy)phenyl or p-(methoxyrhamnosyloxy)phenyl;

$R^4$ is —$CH_2(CO)NH_2$, benzyl, [p-OH]phenyl, or [p-OH, m-Cl]phenyl;

$R^5$ is hydrogen, or mannose;

$R^6$ is 4-epi-vancosaminyl, L-acosaminyl, L-ristosaminyl, or L-actinosaminyl;

$R^7$, as defined below, is attached to the amino group of $R^6$; and $R^7$, $R^{7a}$, and $R^{7b}$ are each independently selected from the group consisting of hydrogen, $(C_2\text{-}C_{16})$alkenyl, $(C_2\text{-}C_{12})$ alkynyl, $(C_1\text{-}C_{12}$ alkyl$)$-$R^8$, $(C_1\text{-}C_{12}$ alkyl$)$-halo, $(C_2\text{-}C_6$ alkenyl$)$-$R^8$, $(C_2\text{-}C_6$ alkynyl$)$-$R^8$, and $(C_1\text{-}C_{12}$ alkyl$)$-O—$R^8$, provided that $R^7$, $R^{7a}$, and $R^{7b}$ are not all hydrogen, and $R^8$ is selected from the group consisting of:

a) multicyclic aryl unsubstituted or substituted with one or more substituents independently selected from the group consisting of:

(i) hydroxy,
(ii) halo,
(iii) nitro,
(iv) $(C_1\text{-}C_6)$alkyl,
(v) $(C_2\text{-}C_6)$alkenyl,
(vi) $(C_2\text{-}C_6)$alkynyl,
(vii) $(C_1\text{-}C_6)$alkoxy,
(viii) halo-$(C_1\text{-}C_6)$alkyl,
(ix) halo-$(C_1\text{-}C_6)$alkoxy,
(x) carbo-$(C_1\text{-}C_6)$alkoxy,
(xi) carbobenzyloxy,
(xii) carbobenzyloxy substituted with $(C_1\text{-}C_6)$alkyl, $(C_1\text{-}C_6)$alkoxy, halo, or nitro,
(xiii) a group of the formula —$S(O)_{n'}$—$R^9$, wherein n' is 0-2 and $R^9$ is $(C_1\text{-}C_6)$alkyl, phenyl, or phenyl substituted with $(C_1\text{-}C_6)$alkyl, $(C_1\text{-}C_6)$alkoxy, halo, or nitro, and
(xiv) a group of the formula —$C(O)N(R^{10})_2$ wherein each $R^{10}$ substituent is independently hydrogen, $(C_1\text{-}C_6)$-alkyl, $(C_1\text{-}C_6)$-alkoxy, phenyl, or phenyl substituted with $(C_1\text{-}C_6)$-alkyl, $(C_1\text{-}C_6)$-alkoxy, halo, or nitro;

b) heteroaryl unsubstituted or substituted with one or more substituents independently selected from the group consisting of:

(i) halo,
(ii) $(C_1\text{-}C_6)$alkyl,
(iii) $(C_1\text{-}C_6)$alkoxy,
(iv) halo-$(C_1\text{-}C_6)$alkyl,
(v) halo-$(C_1\text{-}C_6)$alkoxy,
(vi) phenyl,
(vii) thiophenyl,
(viii) phenyl substituted with halo, $(C_1\text{-}C_6)$alkyl, $(C_2\text{-}C_6)$ alkenyl, $(C_2\text{-}C_6)$alkynyl, $(C_1\text{-}C_6)$alkoxy, or nitro,
(ix) carbo-$(C_1\text{-}C_6)$alkoxy,
(x) carbobenzyloxy,
(xi) carbobenzyloxy substituted with $(C_1\text{-}C_6)$alkyl, $(C_1\text{-}C_6)$alkoxy, halo, or nitro,
(xii) a group of the formula —$S(O)_{n'}$—$R^9$, as defined above,
(xiii) a group of the formula —$C(O)N(R^{10})_2$ as defined above, and
(xiv) thienyl;

c) a group of the formula:

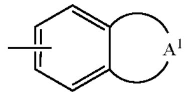

wherein $A^1$ is —$OC(A^2)_2$-$C(A^2)_2$-O—, —O—$C(A^2)_2$-O—, —$C(A^2)_2$-O—, or —$C(A^2)_2$-$C(A^2)_2$-$C(A^2)_2$-$C(A^2)_2$-, and each $A^2$ substituent is independently selected from hydrogen, $(C_1\text{-}C_6)$-alkyl, $(C_1\text{-}C_6)$alkoxy, and $(C_4\text{-}C_{10})$cycloalkyl;

d) a group of the formula:

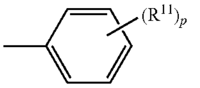

wherein p is from 1 to 5; and $R^{11}$ is independently selected from the group consisting of:

(i) hydrogen,
(ii) nitro,
(iii) hydroxy,
(iv) halo,
(v) $(C_1\text{-}C_8)$alkyl,
(vi) $(C_1\text{-}C_8)$alkoxy,
(vii) $(C_9\text{-}C_{12})$alkyl,
(viii) $(C_2\text{-}C_8)$alkynyl,
(ix) $(C_9\text{-}C_{12})$alkoxy,
(x) $(C_1\text{-}C_3)$alkoxy substituted with $(C_1\text{-}C_3)$alkoxy, hydroxy, halo$(C_1\text{-}C_3)$alkoxy, or $(C_1\text{-}C_4)$alkylthio,
(xi) $(C_2\text{-}C_5)$alkenyloxy,
(xii) $(C_2\text{-}C_{13})$alkynyloxy
(xiii) halo-$(C_1\text{-}C_6)$alkyl,
(xiv) halo-$(C_1\text{-}C_6)$alkoxy,
(xv) $(C_2\text{-}C_6)$alkylthio,
(xvi) $(C_2\text{-}C_{10})$alkanoyloxy,
(xvii) carboxy-$(C_2\text{-}C_4)$alkenyl,
(xviii) $(C_1\text{-}C_3)$alkylsulfonyloxy,
(xix) carboxy-$(C_1\text{-}C_3)$alkyl,
(xx) N—[di$(C_1\text{-}C_3)$-alkyl]amino-$(C_1\text{-}C_3)$alkoxy,
(xxi) cyano-$(C_1\text{-}C_6)$alkoxy, and
(xxii) diphenyl-$(C_1\text{-}C_6)$alkyl, with the proviso that when $R^{11}$ is $(C_1\text{-}C_8)$alkyl, $(C_1\text{-}C_8)$ alkoxy, or halo, p must be greater or equal to 2, or when $R^7$ is $(C_1\text{-}C_3$ alkyl$)$-$R^8$ then $R^{11}$ is not hydrogen, $(C_1\text{-}C_8)$alkyl, $(C_1\text{-}C_8)$alkoxy, or halo;

e) a group of the formula:

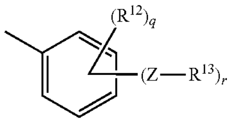

wherein q is 0 to 4; $R^{12}$ is independently selected from the group consisting of:

(i) halo,
(ii) nitro,
(iii) ($C_1$-$C_6$)alkyl,
(iv) ($C_1$-$C_6$)alkoxy,
(v) halo-($C_1$-$C_6$)alkyl,
(vi) halo-($C_1$-$C_6$)alkoxy,
(vii) hydroxy, and
(vii) ($C_1$-$C_6$)thioalkyl, r is 1 to 5; provided that the sum of q and r is no greater than 5;

Z is selected from the group consisting of:

(i) a single bond,
(ii) divalent ($C_1$-$C_6$)alkyl unsubstituted or substituted with hydroxy, ($C_1$-$C_6$)alkyl, or ($C_1$-$C_6$)alkoxy,
(iii) divalent ($C_2$-$C_6$)alkenyl,
(iv) divalent ($C_2$-$C_6$)alkynyl, and
(v) a group of the formula —$(C(R^{14})_2)_s$—$R^{15}$— or —$R^{15}$—$(C(R^{14})_2)_s$—, wherein s is 0-6; wherein each $R^{14}$ substituent is independently selected from hydrogen, ($C_1$-$C_6$)-alkyl, or ($C_4$-$C_{10}$)cycloalkyl; and $R^{15}$ is selected from —O—, —S—, —SO—, —$SO_2$—, —$SO_2$—O—, —C(O)—, —OC(O)—, —C(O)O—, —NH—, —N($C_1$-$C_6$ alkyl)-, and —C(O)NH—, —NHC(O)—, N═N;

$R^{13}$ is independently selected from the group consisting of:

(i) ($C_4$-$C_{10}$)heterocyclyl,
(ii) heteroaryl,
(iii) ($C_4$-$C_{10}$)cycloalkyl unsubstituted or substituted with ($C_1$-$C_6$)alkyl, and
(iv) phenyl unsubstituted or substituted with 1 to 5 substituents independently selected from: halo, hydroxy, nitro, ($C_1$-$C_{10}$)alkyl, ($C_1$-$C_{10}$)alkoxy, halo-($C_1$-$C_3$) alkoxy, halo-($C_1$-$C_3$)alkyl, ($C_1$-$C_3$)alkoxyphenyl, phenyl, phenyl-($C_1$-$C_3$)alkyl, ($C_1$-$C_6$)alkoxyphenyl, phenyl-($C_2$-$C_3$)alkynyl, and ($C_1$-$C_6$)alkylphenyl;

f) ($C_4$-$C_{10}$)cycloalkyl unsubstituted or substituted with one or more substituents independently selected from the group consisting of:

(i) ($C_1$-$C_6$)alkyl,
(ii) ($C_1$-$C_6$)alkoxy,
(iii) ($C_2$-$C_6$)alkenyl,
(iv) ($C_2$-$C_6$)alkynyl,
(v) ($C_4$-$C_{10}$)cycloalkyl,
(vi) phenyl,
(vii) phenylthio,
(viii) phenyl substituted by nitro, halo, ($C_1$-$C_6$)alkanoyloxy, or carbocycloalkoxy, and
(ix) a group represented by the formula —Z—$R^{13}$ wherein Z and $R^{13}$ are as defined above; and g) a group of the formula:

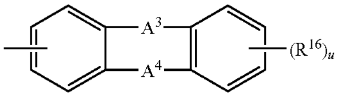

wherein $A^3$ and $A^4$ are each independently selected from (i) a bond,
(ii) —O—,
(iii) —$S(O)_t$—, wherein t is 0 to 2,
(iv) —$C(R^{17})_2$—, wherein each $R^{17}$ substituent is independently selected from hydrogen, ($C_1$-$C_6$)alkyl, hydroxy, ($C_1$-$C_6$)alkyl, ($C_1$-$C_6$)alkoxy, or both $R^{17}$ substituents taken together are 0,
(v) —$N(R^{18})_2$—, wherein each $R^{18}$ substituent is independently selected from hydrogen; ($C_1$-$C_6$)alkyl; ($C_2$-$C_6$) alkenyl; ($C_2$-$C_6$)alkynyl; ($C_4$-$C_{10}$)cycloalkyl; phenyl; phenyl substituted by nitro, halo, ($C_1$-$C_6$)alkanoyloxy; or both $R^{18}$ substituents taken together are ($C_4$-$C_{10}$)cycloalkyl;

$R^{16}$ is $R^{12}$ or $R^{13}$ as defined above; and u is 0-4.

The glycopeptide antibiotics of the present invention include each of those disclosed in U.S. Pat. No. 5,840,684, incorporated herein by reference in its entirety.

Oritavancin (also termed N-(4-(4-chlorophenyl)benzyl) A82846B and LY333328) has the following Formula III:

Formula III

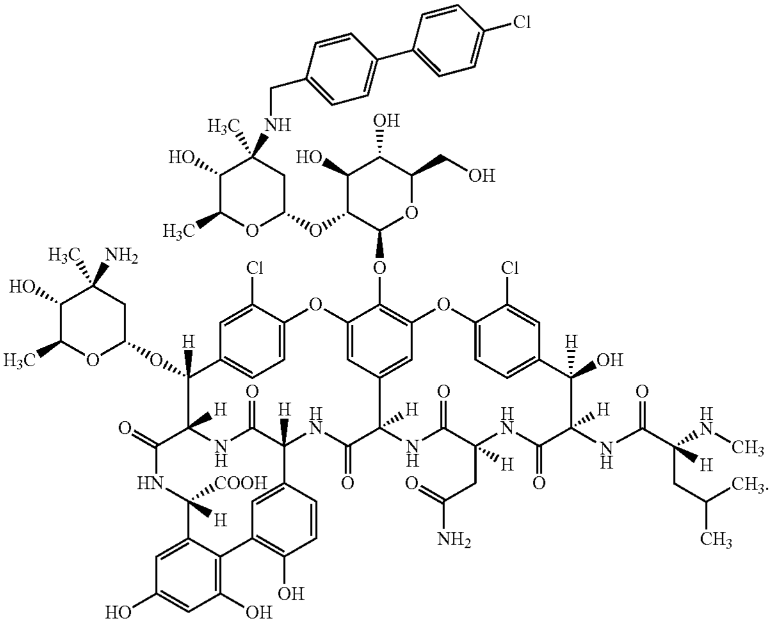

The alkyl substituents recited herein denote substituted or unsubstituted, straight or branched chain hydrocarbons of the length specified. The term "alkenyl" refers to a substituted or unsubstituted, straight or branched alkenyl chain of the length specified herein. The term "alkynyl" refers to a substituted or unsubstituted, straight or branched alkynyl chain of the length specified herein.

The alkoxy substituents recited herein represent an alkyl group attached through an oxygen bridge. The term "alkenoxy" represents an alkenyl chain of the specified length attached to an oxygen atom.

The term "multicyclic aryl" means a stable, saturated or unsaturated, substituted or unsubstituted, 9 to 10 membered organic fused bicyclic ring; a stable, saturated or unsaturated, substituted or unsubstituted 12 to 14 membered organic fused tricyclic ring; or a stable, saturated or unsaturated, substituted or unsubstituted 14 to 16 membered organic fused tetracyclic ring. The bicyclic ring may have 0 to 4 substituents, the tricyclic ring may have 0 to 6 substituents, and the tetracyclic ring may have 0 to 8 substituents. Typical multi-cyclic aryls include fluorenyl, napthyl, anthranyl, phenanthranyl, biphenylene and pyrenyl.

The term "heteroaryl" represents a stable, saturated or unsaturated, substituted or unsubstituted, 4 to 7 membered organic monocyclic ring having a hetero atom selected from S, O, and N; a stable, saturated or unsaturated, substituted or unsubstituted, 9 to 10 membered organic fused bicyclic ring having 1 to 2 hetero atoms selected from S, O, and N; or a stable, saturated or unsaturated, substituted or unsubstituted, 12 to 14 membered organic fused tricyclic ring having a hetero atom selected from S, O, and N. The nitrogen and sulfur atoms of these rings are optionally oxidized, and the nitrogen hetero atoms are optionally quarternized. The monocyclic ring may have 0 to 5 substituents. The bicyclic ring may have 0 to 7 substituents, and the tricyclic ring may have 0 to 9 substituents. Typical heteroaryls include quinolyl, piperidyl, thienyl, piperonyl, oxafluorenyl, pyridyl and benzothienyl and the like.

The term "($C_4$-$C_{10}$)cycloalkyl" embraces substituents having from four to ten carbon atoms, such as cyclobutyl, cyclopentyl, cyclohexyl, and cycloheptyl which may be unsubstituted or substituted with substituents such as alkyl and phenyl. This term also embraces $C_5$ to $C_{10}$ cycloalkenyl groups such as cyclopentenyl and cyclohexenyl. The term "($C_4$-$C_{10}$)cycloalkyl" also embraces bicyclic and tricyclic cycloalkyls such as bicyclopentyl, bicylohexyl, bicycloheptyl, and adamantyl.

The term "alkanoyloxy" represents an alkanoyl group attached through an oxygen bridge. These substituents may be substituted or unsubstituted, straight, or branched chains of the specified length.

The term "cyano-($C_1$-$C_6$) alkoxy" represents a substituted or unsubstituted, straight or branched alkoxy chain having from one to six carbon atoms with a cyano moiety attached to it.

The term "divalent ($C_1$-$C_6$) alkyl" represents an unsubstituted or substituted, straight or branched divalent alkyl chain having from one to six carbon atoms. Typical divalent ($C_1$-$C_6$) alkyl groups include methylene, ethylene, propylene, isopropylene, butylene, isobutylene, secbutylene, t-butylene, pentylene, neo-pentylene, and hexylene. Such divalent ($C_1$-$C_6$) alkyl groups may be substituted with substituents such as alkyl, alkoxy, and hydroxy.

The term "divalent ($C_2$-$C_6$)alkenyl" represents a straight or branched divalent alkenyl chain having from two to six carbon atoms. Typical divalent ($C_2$-$C_6$) alkenyl include ethenyl, 1-propenyl, 2-propenyl, 1-butenyl, 2-butenyl and the like.

The term "divalent ($C_2$-$C_6$) alkynyl" represents a straight or branched divalent alkynyl chain having from two to six carbon atoms. Typical divalent ($C_2$-$C_6$) alkynyl include ethynylene, 1-propynylene, 2-propynylene, 1-butynylene, 2-butynylene and the like.

The term "halo" represents chloro, fluoro, bromo or iodo.

The term "halo-($C_1$-$C_6$)alkyl" represents a straight or branched alkyl chain having from one to six carbon atoms with from 0 to 3 halogen atoms attached to each carbon.

Typical halo-($C_1$-$C_6$) alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

The term "halo-($C_1$-$C_6$)alkoxy" represents a straight or branched alkoxy chain having from one to six carbon atoms with from 0 to 3 halogen atoms attached to each carbon.

Typical halo-($C_1$-$C_6$) alkoxy groups include chloromethoxy, 2-bromoethoxy, 1-chloroisopropoxy, 3-fluoropropoxy, 2,3-dibromobutoxy, 3-chloroisobutoxy, iodo-t-butoxy, trifluoromethoxy, and the like.

The term "heterocyclyl" embraces saturated groups having three to ten ring members and which heterocyclic ring contains a hetero atom selected from oxygen, sulfur and nitrogen, examples of which are piperazinyl, morpholino, piperdyl, methylpiperdyl, azetidinyl, and aziridinyl.

The glycopeptide antibiotics of the present invention, including oritavancin, may be used per se or in the form of a pharmaceutically acceptable salt, hydrate, solvate or mixtures thereof. The term "pharmaceutically acceptable salt" refers to non-toxic acid addition salts derived from inorganic and organic acids. In a preferred embodiment, a pharmaceutically acceptable salt of oritavancin is oritavancin diphosphate.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counter-ion forming a part of any salt of this invention is not of a critical nature, so long as the salt as a whole is pharmacologically acceptable and as long as the counter-ion does not contribute undesired qualities to the salt as a whole.

Means for the preparation of the glycopeptide antibiotics, including oritavancin and analogs thereof, may be found, for example, in U.S. Pat. No. 5,840,684, incorporated herein by reference in its entirety.

As used herein, a "subject" refers to an animal, such as a mammal, preferably a human. The subject may have an asymptomatic *B. anthracis* infection, a symptomatic *B. anthracis* infection, may be at risk for developing a *B. anthracis* infection, or may be at greater risk than the general population for developing a *B. anthracis* infection. Examples of subjects having a higher risk for *B. anthracis* infection include patients with impaired immune function (e.g., immunoglobulin deficiency, splenic dysfunction, splenectomy, HIV infection, impaired leukocyte function, hemoglobinopathies), the elderly, people with certain malignancies (e.g., multiple myeloma, chronic lympocytic leukemia, lymphoma), people at increased occupational risk (e.g., public services workers, such a fire, water, sanitary, police, medical, and laboratory workers, hospital workers, public servants such as mail-room workers and government employees, members of the press and media), people in closed populations (e.g., prisons, military, nursing homes) and those that have immunological deficiencies that might enhance their susceptibility to bacterial infection.

The methods of the present invention may be performed in vivo, in vitro or ex vivo. The in vitro methods are exemplified, but not limited to, methods performed in a laboratory setting, such as in a cell culture, as well as methods performed on inert objects such as laboratory or hospital equipment and devices, surfaces such as countertops and bench tops. The ex vivo methods are exemplified, but not limited to, methods performed on the surface of the human body, such as on the hands.

In each of the methods of the present invention, the glycopeptide antibiotic may be used alone, in combination with one or more additional glycopeptides, such as vancomycin, in combination with one or more other antibiotic agents or as a combination of two or more glycopeptides and one or more other antibiotic agents. In particular, in each of the methods of the present invention oritavancin may be (a) used alone, (b) used in combination with one or more additional glycopeptides, such as vancomycin, (c) used in combination with one or more other antibiotic agents, or (d) used as a combination of (i) oritavancin, (ii) one or more other glycopeptides, and (iii) one or more other antibiotic agents. The other antibiotic agents include fluoroquinolones (including ciprofloxacin), tetracyclines (including doxycycline), macrolides (including erythromycin, cethromycin, azithromycin and clarithromycin), β3-lactams (including penicillin, imipenem and ampicillin), ansamycins (including rifampin), phenicols (including chloramphenicol), streptogramins (including quinupristin-dalfopristin), aminoglycosides (including gentamicin), oxazolidinones (including linezolid), tetracyclines, glycylglycines (including tigecycline), cyclic lipopeptides (including daptomycin) and lincosamines (including clindamycin).

The pharmaceutical compositions of the present invention comprise one or more glycopeptide antibiotics, and one or more of a carrier, diluent and excipient. A preferred pharmaceutical composition comprises oritavancin and one or more of a carrier, diluent and excipient. The present invention also includes pharmaceutical compositions comprising oritavancin (a) in combination with one or more additional glycopeptides, such as vancomycin, (b) in combination with one or more other antibiotic agents, including fluoroquinolones, such as ciprofloxacin, doxycycline, erythromycin, or penicillin, and (c) a combination of (i) oritavancin, (ii) one or more other glycopeptides, and (iii) one or more other antibiotic agents, together with one or more of a carrier, diluent and excipient.

Suitable carriers, diluents and excipients are well known to those skilled in the art and include saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium.

Carriers include cornstarch, gelatin, lactose, sucrose, microcrystalline cellulose, kaolin, mannitol, dicalcium phosphate, sodium chloride, alginic acid, croscarmellose sodium, and sodium starch glycolate.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweetners, perfuming agents, flavouring agents, coloring agents, administration aids, and combinations thereof.

The particular carrier, diluent or excipient used will depend upon the means and purpose for which the active ingredient is being applied.

Tonicity agents made be used as pharmaceutically acceptable excipients and serve to make the solution compatible with blood. Tonicity agents are particularly desirable in injectable formulations.

The pharmaceutical compositions and glycopeptide antibiotics of the present invention may be formulated, for example, for oral, sublingual, intranasal, intraocular, rectal, transdermal, mucosal, topical or parenteral administration for the treatment, prophylaxis or prevention of *B. anthracis* infection. Parenteral modes of administration include, without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intraarticular (joint), intrasynovial (joint fluid area), intracranial, intraspinal, and intrathecal (spinal fluids). Any known device useful for parenteral injection or infusion of drug formulations can be used to effect such administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophomm), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of glycopeptide antibiotics can be a ready-to-use solution of the glycopeptide antibiotic in a suitable carrier in sterile, hermetically sealed ampoules or in sterile pre-loaded syringes. The suitable carrier optionally comprises any of the above-mentioned excipients.

Alternatively, the unit dosage of the glycopeptide antibiotics of the present invention can be in a concentrated liquid, powder or granular form for ex tempore reconstitution in the appropriate pharmaceutically acceptable carrier at the time of delivery, and dilution where appropriate. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose or Ringer's™ solution.

In intramuscular preparations, a sterile formulation of the pharmaceutical compositions of the present invention can be dissolved and administered in a pharmaceutical diluent such as Water-for-Injection (WFI), physiological saline or 5% dextrose. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical composition. Solid formulations such as tablets and capsules are particularly useful. Sustained released or enterically coated preparations may also be devised. For pediatric and geriatric applications, suspension, syrups or elixirs, wafers and chewable tablets are especially suitable.

For therapeutic purposes, the tablets and capsules can contain, in addition to the glycopeptide antibiotics, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), coloring agents, sweetening agents, and preservatives. Carriers may also include coating excipients such as glyceryl monostearate or glyceryl distearate, to delay absorption in the gastrointestinal tract.

In a particular oral formulation, the glycopeptide antibiotics of the present invention may be in the form of a capsule containing the glycopeptide antibiotic, gelatin, iron oxide, polyethylene glycol, titanium dioxide, and one or more other inactive ingredients. Suitable amounts of the glycopeptide antibiotic in the capsule may range from 10 to 1000 mg, with preferred amounts including 100, 125, 150, 175, 200, 225, 250, 275, 300, 350, 400, 450 or 500 mg of the glycopeptide antibiotic.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use, the pharmaceutical compositions of present invention can also be prepared in suitable forms to be applied to the skin, or mucus membranes of the nose and throat, and can take the form of creams, ointments, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride.

The term "dose", "unit dose", "unit dosage", or "effective dose" refers to physically discrete units that contain a predetermined quantity of active ingredient calculated to produce a desired therapeutic effect.

The therapeutically effective amount of the glycopeptide antibiotics of the present invention vary depending upon the physical characteristics of the patient, the severity of the patient's symptoms, the period of time since infection, the formulation and the means used to administer the drug. The specific dose for a given patient is usually set by the judgment of the attending physician. However, a therapeutically effective amount of the glycopeptide antibiotics of the present invention, including oritavancin, is typically between about 0.5 mg/kg body weight to 500 mg/kg body weight, preferably from 1 to 100 mg/kg, more preferably from 3 to 50 mg/kg, 3 to 30 mg/kg or 3 to 15 mg/kg, regardless of the formulation. In equally preferred embodiments, a therapeutically effective amount is about 0.5, 1, 3, 5, 10, 15, 20, 25, 30, 35, 40, 45 or 50 mg/kg body weight, regardless of the formulation. In some situations, a dose less than 0.5 mg/kg body weight may be effective.

The amounts of the glycopeptide antibiotics of the present invention sufficient to inhibit the growth of *B. anthracis* bacteria will also vary depending on the environment in which the bacteria is contacted with the glycopeptide antibiotic, and the form of the bacteria (e.g., vegetative cell or spore). However, in general the amount of the glycopeptide antibiotic, including oritavancin, sufficient to inhibit the growth of *B. anthracis* bacteria is between about 0.001 to 100 μg/ml, preferably 0.01 to 10 μg/ml, more preferably 0.01 to 1 μg/ml.

Suitable frequencies for contacting the bacteria with a glycopeptide of the invention, or administering a glycopeptide of the invention to a subject, may vary based on whether administration is for the purposes of inhibition, treatment, prophylaxis or prevention. Administration frequencies for the treatment of a subject having a *B. anthracis* infection, for prophylaxis, or for prevention of *B. anthracis* infection include 4, 3, 2 or once daily, every other day, every third day, every fourth day, every fifth day, every sixth day, once weekly, every eight days, every nine days, every ten days, bi-weekly, monthly and bimonthly, and less frequent doses including a single dose.

As used herein, the terms "inhibit", "inhibiting" and "inhibition" have their ordinary and customary meanings, and include one or more of inhibiting colonization of *B. anthracis*, inhibiting growth of a vegetative form of *B. anthracis*, inhibiting a function of a vegetative form of *B. anthracis*, inhibiting propagation of a vegetative form of *B. anthracis*, inhibiting *B. anthracis* sporulation, inhibiting activation of a *B. anthracis* spore, inhibiting germination of a *B. anthracis* spore, and inhibiting outgrowth of a *B. anthracis* spore. Such inhibition is an inhibition of about 1% to about 100% of the particular activity versus activity in the absence of the glycopeptide antibiotic. Preferably, the inhibition is an inhibition of 100%, 99%, 98%, 97%, 96%, 95%, 90%, 80%, 70%, 60%, 50%, 40%, 30%, 20%, 10%, 5% or 1% of the activity versus activity in the absence of the glycopeptide antibiotic. As used herein, the inhibition lasts at least 0.5, 1, 2, 3, 4, 5, 6, 7, 10, 12, 15, 20, 25, 30, 35, 40, 45, 50, 55, 60, or more days after administration of a pharmaceutical composition or glycopeptide antibiotic of the present invention.

The skilled artisan will understand that in methods of inhibiting colonization of a subject by *B. anthracis*, the inhibition generally relates to a decrease in the ability of the population of *B. anthracis* entering the subject to form a productive infection in the subject. Such decrease may result from one or more of an inhibition of *B. anthracis* vegetative cell growth, an inhibition of vegetative cell function, an inhibition of vegetative cell propagation, an inhibition of *B. anthracis* sporulation, an inhibition of activation of *B. anthracis* spores, an inhibition of germination of *B. anthracis* spores, and/or an inhibition of outgrowth of *B. anthracis* spores. Such inhibition is an inhibition of about 1% to about 100% of the particular activity versus activity in the absence of the glycopeptide antibiotic. Preferably, the inhibition is an inhibition of 100%, 99%, 98%, 97%, 96%, 95%, 90%, 80%, 70%, 60%, 50%, 40%, 30%, 20%, 10%, 5% or 1% of the activity versus activity in the absence of the glycopeptide antibiotic. As used herein, the inhibition of colonization lasts at least 0.5, 1, 2, 3, 4, 5, 6, 7, 10, 12, 15, 20, 25, 30, 35, 40, 45, 50, 55, 60, or more days after administration of a pharmaceutical composition or glycopeptide antibiotic of the present invention.

As used herein, "spore" refers to both the conventionally used terms "spore" and "endospore."

As used herein, the terms "treating" and "treatment" have their ordinary and customary meanings, and include one or more of, ameliorating a symptom of *B. anthracis* infection in a subject, blocking or ameliorating a recurrence of a symptom of *B. anthracis* infection in a subject, decreasing in severity and/or frequency a symptom of *B. anthracis* infection in a subject, stasis, decreasing, or inhibiting growth of a vegetative form of *B. anthracis* in a subject, inhibiting *B. anthracis* sporulation, inhibiting activation of a *B. anthracis* spore in a subject, inhibiting germination of a *B. anthracis* spore in a subject, and inhibiting outgrowth of a *B. anthracis* spore in a subject. Treatment means ameliorating, blocking, reducing, decreasing or inhibiting by about 1% to about 100% versus a subject to which a pharmaceutical composition or glycopeptide antibiotic of the present invention has not been administered. Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1% versus a subject to which a pharmaceutical composition or glycopeptide antibiotic of the present invention has not been administered. The treatment may begin prior to, concurrent with, or after the onset of clinical symptoms of the infection.

As used herein, the terms "preventing" and "prevention" have their ordinary and customary meanings, and includes one or more of preventing colonization of *B. anthracis* in a subject, preventing infection of *B. anthracis* in a subject, preventing an increase in the growth of a population of *B. anthracis* in a subject, preventing activation, germination or outgrowth of *B. anthracis* spores in a subject, preventing sporulation of *B. anthracis* in a subject, preventing development of a disease caused by *B. anthracis* in a subject, and preventing symptoms of a disease caused by *B. anthracis* in a subject. As used herein, the prevention lasts at least 0.5, 1, 2, 3, 4, 5, 6, 7, 10, 12, 15, 20, 25, 30, 35, 40, 45, 50, 55, 60, or more days after administration of a pharmaceutical composition or glycopeptide antibiotic of the present invention.

As used herein, "prophylaxis" includes inhibiting the development of a productive or progressive infection by *B. anthracis* in a subject, where the prophylaxis lasts at least 0.5, 1, 2, 3, 4, 5, 6, 7, 10, 12, 15, 20, 25, 30, 35, 40, 45, 50, 55, 60, or more days after administration of a pharmaceutical composition or glycopeptide antibiotic of the present invention. Inhibition against development of a productive or progressive infection by *B. anthracis* infection means that the severity of a *B. anthracis* infection in a subject is reduced by about 1% to about 100% versus a subject to which a pharmaceutical composition or glycopeptide antibiotic of the present invention has not been administered. Preferably, the reduction in severity is a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of *B. anthracis* present in a subject, the length of time that *B. anthracis* can be detected in a subject, and/or the severity of a symptom of *B. anthracis* infection, among other factors.

In the methods of the present invention directed to preventing a *B. anthracis* infection and inhibiting colonization by *B. anthracis*, the glycopeptide antibiotic is administered to the subject less than about 60, 50, 40, 30, 25, 20, 15, 12, 10, 9, 8, 7, 6, 5, 4 or 3 days prior to the risk of exposure to *B. anthracis*, or less than about 60, 48, 36, 24, 12, 8, 10, 6, 4, 2 or 1 hour prior to the risk of exposure to *B. anthracis*.

In the methods of the present invention directed to treating a *B. anthracis* infection and providing prophylaxis of a *B. anthracis* infection, the glycopeptide antibiotic is administered as quickly as possible following exposure to *B. anthracis*. Preferably, the glycopeptide antibiotic is administered to a subject exposed to *B. anthracis* within 15, 30, 45, 60, 90, or 120 minutes, or within 3, 6, 9, 12, 15, 18, 21, 24, 36, 48, 60 or 72 hours, or within 4, 5, 6, 7, 8, 9, 10, 11, 12, 13, 14, 15, 16, 17, 18, 19, 20, 21, 22, 23, 24 or 25 days, of exposure.

Under some circumstances, the time at which the subject was exposed to *B. anthracis* cannot be determined, and infection by *B. anthracis* is only diagnosed upon the onset of clinical symptoms. Under such circumstances, the glycopeptide antibiotic is administered to a subject within 15, 30, 45, 60, 90, or 120 minutes, or within 3, 6, 9, 12, 15, 18, 21, 24, 36, 48, 60 or 72 hours, or within 4, 5, 6, 7, 8, 9, 10, 11, 12, 13, 14, 15, 16, 17, 18, 19, 20, 21, 22, 23, 24 or 25 days, of the diagnosis of *B. anthracis* infection.

As used herein, the term "bi-weekly" refers to a frequency of every 13-15 days, the term "monthly" refers a frequency of every 28-31 days and "bimonthly" refers a frequency of every 58-62 days.

As used herein, the term "contacting" is meant to broadly refer to bringing a bacterial cell and a molecule of a glycopeptide antibiotic of the present invention into sufficient proximity that the glycopeptide antibiotic can exert an effect on the bacterial cell. The glycopeptide antibiotic may be transported to the location of the bacterial cell, or the glycopeptide antibiotic may be situated in a location to which the bacterial cell travels or is brought into contact. The skilled artisan will understand that the term “contacting” includes physical interaction between a glycopeptide antibiotic and a bacterial cell, as well as interactions that do not require physical interaction.

The present invention includes a kit comprising the pharmaceutical composition or a glycopeptide antibiotic of the present invention and written instructions for its use in treatment, prophylaxis and/or prevention of *B. anthracis* infection. The pharmaceutical composition/glycopeptide antibiotic and written instructions may be in a container, such as a box. The pharmaceutical composition/glycopeptide antibiotic may also be in a smaller container, such as a vial, with the larger container comprising the pharmaceutical composition/glycopeptide antibiotic and written instructions. The smaller container may be instrument for use in administering the pharmaceutical composition/glycopeptide antibiotic to a subject. The pharmaceutical composition/glycopeptide antibiotic may be in a formulation that may be directly administered to a subject.

EXAMPLES

Demonstration of activity of an antibacterial agent, such as a glycopeptide antibiotic, in an animal model is of significant impact to the identification of doses and dose regimens that would provide effective therapy in humans because phase II and phase III clinical trials (on anthrax-infected patients) cannot be conducted for ethical reasons. As such, studies with anthrax-infected animals are critical to approval of agents for anthrax chemotherapy (“Two Animal Rule”, Federal Register. 2002. Fed. Regist. 67:37988-37998; and Guidance for Industry. Inhalational Anthrax [Post-Exposure]—Developing Antimicrobial Drugs. CDER March 2002).

Likewise, characterization of the in vitro activity of an antibacterial agent, such as a glycopeptide antibiotic, against representative bacterial isolates is an important step in predicting whether an antibiotic dose and dose regimen that are efficacious in animals infected with a single test strain may be expected to provide a therapeutic benefit in animals infected with other, disparate isolates of the same organism that are likely to be found outside of the laboratory environment.

Experiment 1

Susceptibility of *B. anthracis* Strains to Oritavancin as Measured by Broth Microdilution Broth microdilution minimum inhibitory concentrations (MICs) were determined for oritavancin against a challenge set of 30 *B. anthracis* strains, including the Ames strain, from the USAMRIID collection. These strains were isolates from human or animal infections throughout the world and represent the eight genotype clades identified by Keim (Keim et al. 2000. *J. Bacteriol.* 182:2928-2936). MICs for comparator antibiotics ciprofloxacin and vancomycin were determined in parallel.

MICs were determined by the broth microdilution method in 96-well plates according to guideline M7-A7 of the Clinical and Laboratory Standards Institute (Clinical and Laboratory Standards Institute (CLSI). 2006a. Methods for Dilution Antimicrobial Susceptibility Tests for Bacteria That Grow Aerobically; Approved Standard—Seventh Edition. CLSI document M7-A7 (ISBN 1-56238-587-9); Clinical and Laboratory Standards Institute, 940 West Valley Road, Suite 1400, Wayne, Pa. 19087) with the exception that 0.002% polysorbate-80 was included in some assays with oritavancin.

Oritavancin diphosphate was dissolved in 0.002% polysorbate-80 in water so as to minimize drug binding to surfaces (Arhin et al. 2007a. Influence of Polysorbate-80 on Susceptibility of gram-positive Bacteria to Oritavancin. $17^{th}$ European Congress of Clinical Microbiology and Infectious Diseases; Munich, Germany, March 31-April 3. Poster # P827; Arhin et al. 2007b. Effect of Polysorbate-80 on Oritavancin Binding to Plastic Surfaces—Implications for Susceptibility Testing. $17^{th}$ European Congress of Clinical Microbiology and Infectious Diseases; Munich, Germany, March 31-April 3. Poster # P1112) and was serially diluted twofold in 50 μL of cation-adjusted Mueller-Hinton broth (CAMHB) with 0.004% polysorbate-80 such that upon inoculation with an equal volume of cells in CAMHB, the final concentration of polysorbate-80 would be 0.002%. To determine the impact, if any, of polysorbate-80 upon oritavancin MICs for *B. anthracis*, a parallel broth microdilution assay was conducted in which oritavancin was dissolved in water and drug dilutions were prepared by serial twofold dilution in CAMHB without polysorbate-80. For assays with polysorbate-80, the range of oritavancin concentrations was 0.002-2 μg/mL based on a final well volume of 100 μL after inoculation; for assays without polysorbate-80, the range of oritavancin concentrations was 0.008-8 μg/mL.

The inoculum was prepared by suspension of colonies from sheep blood agar plates (SBAP) into CAMHB. Suspensions were diluted with CAMHB to a bacterial cell density of 106 colony-forming units (CFU)/ml (conversion factor, $3.82\times10^7$ CFU/ml/OD600 nm). To each well of the 96-well plate, 50 μL of this cell suspension was added for a final inoculum of approximately $5\times10^4$ CFU/well ($5\times10^5$ CFU/mL) and a final polysorbate-80 concentration of 0.002%, when present. After 18 h incubation at 35° C. the plates were read visually and verified at 600 nm (M1 Microplate Reader, Molecular Designs Inc). The test was considered valid if (i) the growth control wells had visible growth, (ii) the CAMHB and antibiotic control wells had no growth or precipitate, and (iii) the dilution plates of the original inoculum had pure cultures yielding final counts of $10^5$ to $10^7$ CFU/mL.

Quality control of oritavancin dilutions was established using *Staphylococcus aureus* ATCC 29213 according to CLSI (CLSI, 2006b, supra) recommendations with polysorbate-80 at 0.002% throughout.

As shown in FIG. 1, the results clearly demonstrated an on-average decrease of four doubling dilutions for oritavancin MICs for *B. anthracis* when oritavancin susceptibilities were determined with polysorbate-80: the oritavancin $MIC_{90}$ (concentration at which 90% of the organisms in the group are inhibited) with polysorbate-80 (0.12 μg/mL; n=30) was 16-fold lower than the $MIC_{90}$ in the absence of polysorbate-80. This result is consistent with results from previous in vitro studies which showed a 16- to 32-fold reduction in oritavancin $MIC_{90}$ for staphylococci and enterococci (Arhin et al., 2007a; 2007b; supra). The oritavancin MIC for the Ames strain specifically shifted from 1 μg/mL to 0.015 μg/mL in the presence of polysorbate-80. The one “outlier” strain in both determinations (oritavancin MIC, 4 μg/mL without polysorbate-80 and 1 μg/mL with polysorbate-80; FIG. 1) is known to be a high capsule producer. Minimum bactericidal concentrations (MBCs) are impossible to determine accurately for *B. anthracis* because of the presence of spores.

Experiment 2

Oritavancin Pharmacokinetics and Dosing Determinations

The intravenous (i.v.) route of administration has been used for oritavancin in all clinical trials to date. However, because multiple doses of the test and control agents are often required during therapy in the mouse model of inhalation anthrax, the i.p. route is the most convenient route of administration since multiple i.p. administrations of test agent and comparators are generally well-tolerated by the animal. A pharmacokinetics (PK) study was therefore performed in mice to compare oritavancin exposure in plasma following administration of a single dose of oritavancin by the i.v. and i.p. routes.

All in vivo studies were performed in accordance with guidelines set by the USAMRIID Institutional Animal Care and Use Committee.

Oritavancin for injection for both PK studies and studies of efficacy was formulated by dissolving oritavancin diphosphate (Abbott Lot 01005PP00; assay potency (volatile-free basis), 84.9%) in 5% dextrose in water (D5W) to the appropriate concentration followed by sterile filtration.

Mice (female CD-1; body weight 19-21 g) received a single bolus dose of 32 mg/kg oritavancin in dosing formulation (as described above) either i.v. or i.p. and blood was collected by cardiac puncture (n=3 mice/time point). Levels of oritavancin in plasma were determined by a validated LC/MS method. PK parameters were calculated using WinNonlin software (Pharsight). All parameters were calculated using the non-compartmental model.

Figure 2:
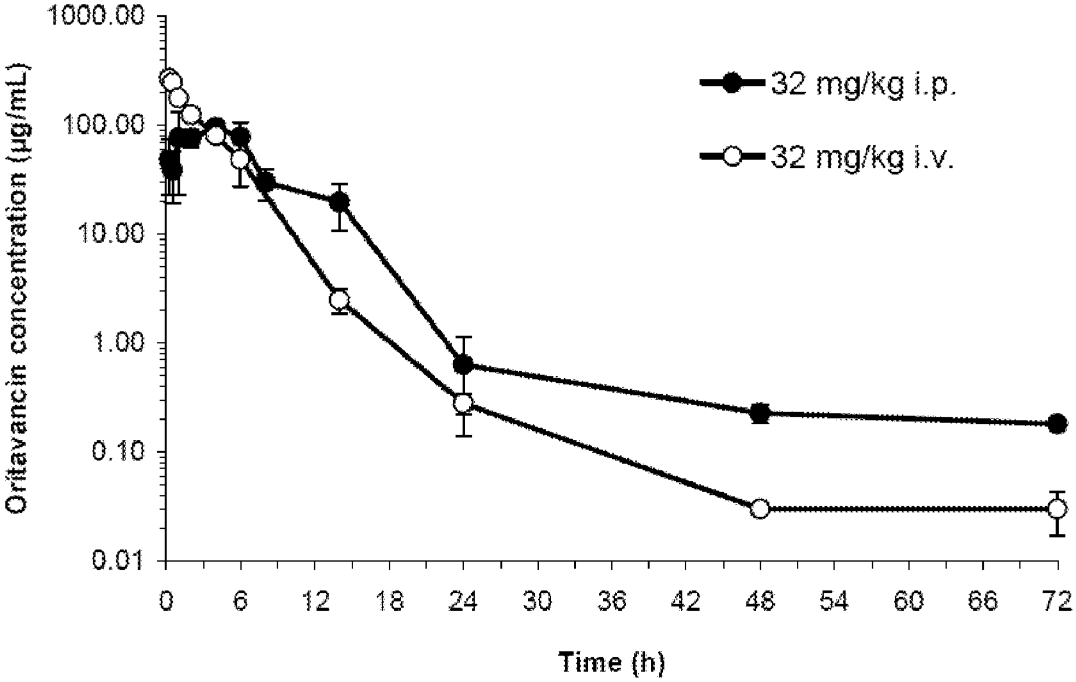
FIG. 2 depicts oritavancin pharmacokinetics in mouse plasma following bolus administration of a single 32 mg/kg dose by either the i.v. or i.p. route.

The plasma concentration-time profile of oritavancin following single dose bolus i.v. administration concurred with that from previous analyses of oritavancin pharmacokinetics (PK) in mice (Phillips. 1996. Plasma Concentrations of LY333328 in Male Fischer 344 Rats Administered a Single Intravenous Injection of 30 mg/kg (free base) of LY333328 Diphosphate (R31595). ADME Report 11. Eli Lilly and Company; Boylan et al. 2003. *Antimicrob Agents Chemother,* 47(5):1700-6; Lehoux et al. 2007. Efficacy of oritavancin in a mouse model of *Streptococcus pneumoniae* pneumonia. 17th European Congress of Clinical Microbiology and Infectious Diseases and 25th International Congress of Chemotherapy, Munich, Germany, March 31-Apr. 3, 2007. Poster P-1781): after administration of a single i.v. dose of oritavancin at 32 mg/kg to mice, the plasma concentration of oritavancin remained above the MIC for the Ames strain of *B. anthracis* (0.06 μg/mL with polysorbate-80) for between 24 to 48 hours (FIG. 2). Observed peak ($C_{max}$), time-to-peak ($T_{max}$), and area under the concentration-time curve from 0.25 to 72 h ($AUC_{0.25\text{-}72h}$) were 270 μg/mL, 0.25 h, and 950 μg*h/mL, respectively, for the i.v. route and 95 μg/mL, 4 h, and 840 μg*h/mL, respectively, for the i.p. route. Thus while the peak level in plasma was significantly higher following i.v. versus i.p. administration (and was likely underestimated for the i.v. route since a timepoint immediately after the end of bolus administration was not included), and while $T_{max}$ was delayed to 4 h following i.p. administration, oritavancin exposure (measured here as $AUC_{0.25\text{-}72h}$) was found to be similar for the two routes.

Parameters of the Mouse Inhalation Anthrax Model Oritavancin Efficacy Testing, and Determination of Bacterial Burden in Tissue For all antibiotic efficacy trials, Ames spores of *B. anthracis* were used for an aerosol challenge of 50-75 $LD_{50}$ ($LD_{50}$=3.4×10$^4$ spores) (Heine et al. 2007. *Antimicrob. Agents Chemother.* 51: 1373-1379). Negative control animals (n=10) either received no treatment or vehicle alone. A positive control group (n=10) of ciprofloxacin 30 mg/kg intraperitoneally (i.p.), starting 24 h post-challenge, twice daily (q12 h) for 14 days was also routinely included. Oritavancin treatment groups consisted of 10 animals. For all antibiotic efficacy experiments, Kaplan-Meier curves were compared by the log rank test for significance over controls.

Experiment 3

Dose-Ranging Efficacy Studies in the Post-Exposure Prophylaxis Model—Multiple Dose A multiple-dose dose ranging study in the post-exposure prophylaxis anthrax model (Heine et al., 2007, supra) tested oritavancin efficacy when administered i.p. in a range of 0.1, 0.3, 1, 3, 10, and 30 mg/kg q48 h for 14 days. All treatments were initiated 24 hours after challenge and the experiment was terminated at day 29. Clinical signs and survivorship were evaluated daily.

Figure 3:
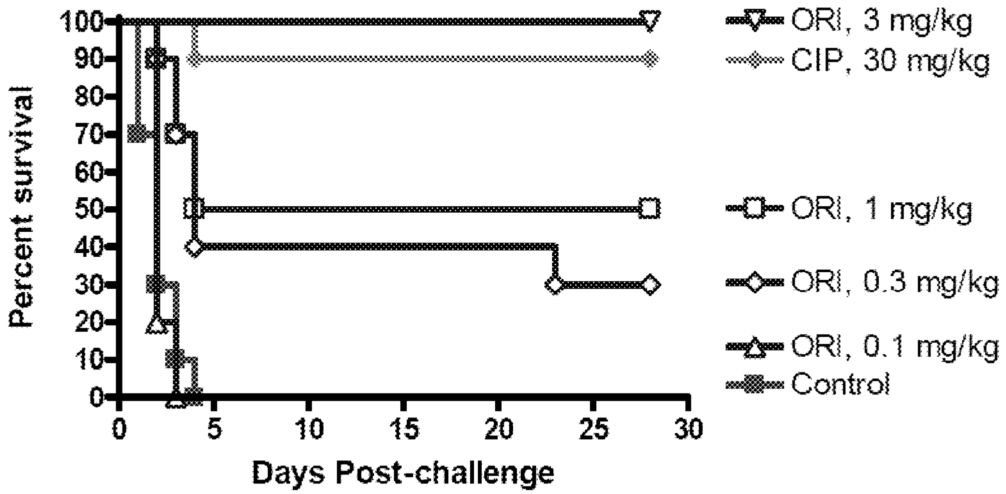
FIG. 3 depicts the proportional survival from multiple dose oritavancin i.p. dose ranging in the post-exposure prophylaxis model of inhalation anthrax. Control animals received no treatment. Animals in the "CIP" group received ciprofloxacin at 30 mg/kg q12 h i.p. for 14 days. Oritavancin ("ORI") doses are indicated in the figure legend and were administered q48 h i.p. for 14 days. All treatments began 24 h post-challenge. Oritavancin doses of 10 and 30 mg/kg administered q48 h i.p. for 14 d provided 100% protection; their corresponding survival curves are not shown.

The multiple-dose dose ranging study showed that i.p. doses of oritavancin each 48 h (q48 h) at 3 mg/kg offered effective post-exposure prophylaxis against a *B. anthracis*, Ames strain aerosol challenge (FIG. 3). A clear dose-response was seen in this study between 0.1 mg/kg oritavancin, which provided no protection, to 1 mg/kg, which provided 50% protection, to 3 mg/kg, which provided 100% protection (FIG. 3). As would be predicted from the protective effect that was seen at 3 mg/kg, oritavancin doses above 3 mg/kg (i.e., 10 and 30 mg/kg) also provided complete protection (Targanta Therapeutics data, on file). In this model, 100% of untreated control mice succumbed to infection by 4 days post-challenge (FIG. 3, "Control" curve) and 90% of animals survived in the group that received ciprofloxacin at 30 mg/kg q12 h for 14 days (FIG. 3, "CIP" curve). The proportional survival seen with untreated and ciprofloxacin-treated animals concurs with literature findings (Heine et al., 2007, supra).

Experiment 4

Dose-Ranging Efficacy Studies in the Post-Exposure Prophylaxis Model—Single Dose Oritavancin was given as a single intravenous (i.v.) dose of 5, 15, or 50 mg/kg. All treatments were initiated 24 hours after challenge and the experiment was terminated at day 30. Clinical signs and survivorship were evaluated daily.

Figure 4:
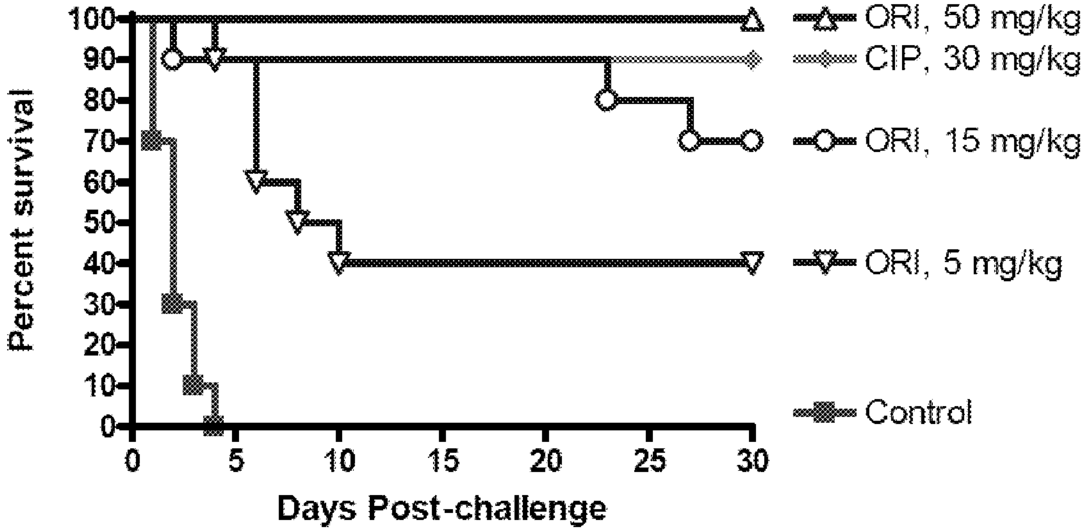
FIG. 4 depicts the proportional survival from single-dose oritavancin i.v. dose ranging in the post-exposure prophylaxis model of inhalation anthrax. Control animals received no treatment. Animals in the "CIP" group received ciprofloxacin at 30 mg/kg q12 h i.p. for 14 days. Single-dose oritavancin ("ORI") doses were administered i.v. and are indicated in the figure legend. All treatments began 24 h post-challenge.

The results demonstrated that a single i.v. dose of oritavancin at 50 mg/kg administered 24 hours after challenge offered 100% protection; furthermore, a significant number of animals (7/10) survived to 30 days with a single i.v. dose of 15 mg/kg oritavancin (FIG. 4). Late deaths in the 15 mg/kg treatment group are most likely due to outgrowth of residual spores still present in the lung tissue, possibly after antibiotic levels dropped below some putative therapeutic threshold. Following the single dose of oritavancin at 50 mg/kg, for which there were no late deaths, oritavancin may have reduced the spore burden to below the infection threshold (Heine et al., 2007, supra) before the level of oritavancin dropped below its therapeutic threshold. Table 1 shows that the spore/tissue load at the termination of the study did not exceed 5×10$^4$ CFU/g tissue in mice treated with oritavancin. Previous experiments have shown that spore/tissue burdens in this range and below are consistent with survival (Heine et al., 2007, supra).

TABLE 1

Post-treatment Spore Counts in Mouse Lung Tissue from Post Exposure Prophylaxis Model of Inhalation Anthrax (Dose Ranging Experiment)

| Treatment | CFU/g tissue[a] |
|---|---|
| Ciprofloxacin 30 mg/kg q12 h × 14 days | $5.20 \times 10^4$ |
| Oritavancin 30 mg/kg i.p. q48 h × 14 days | $1.82 \times 10^4$ |
| Oritavancin 10 mg/kg i.p. q48 h × 14 days | $4.79 \times 10^4$ |
| Oritavancin 3 mg/kg i.p. q48 h × 14 days | $3.68 \times 10^4$ |
| Oritavancin 1 mg/kg i.p. q48 h × 14 days | $2.95 \times 10^4$ |
| Oritavancin 0.3 mg/kg i.p. q48 h × 14 days | $2.80 \times 10^4$ |
| Oritavancin 50 mg/kg i.v. single dose | $3.61 \times 10^4$ |
| Oritavancin 15 mg/kg i.v. single dose | $2.03 \times 10^4$ |
| Oritavancin 5 mg/kg i.v. single dose | $3.50 \times 10^4$ |

[a]Lung tissue collected on day 30 postchallenge

Experiment 5

Multiple Dose Efficacy Study in the Post-Exposure Treatment Model

Delay of start of treatment from 24 hours to 36 or 48 hours post-challenge in the mouse aerosol anthrax model results in dissemination of anthrax into the blood and tissues (Heine et al., 2007, supra). This model has therefore been termed the post-exposure treatment model as it may reflect the need for long courses of therapy after the onset of symptoms to achieve cure in humans.

To determine the efficacy of oritavancin treatment post-symptom development (Heine et al., 2007, supra), a study was performed in which initiation of therapy with oritavancin was delayed to either 36 or 48 h post-challenge. Oritavancin was administered at 10 mg/kg i.p. q48 h for 14 days; clinical signs and survivorship were evaluated daily until day 31.

Figure 5:
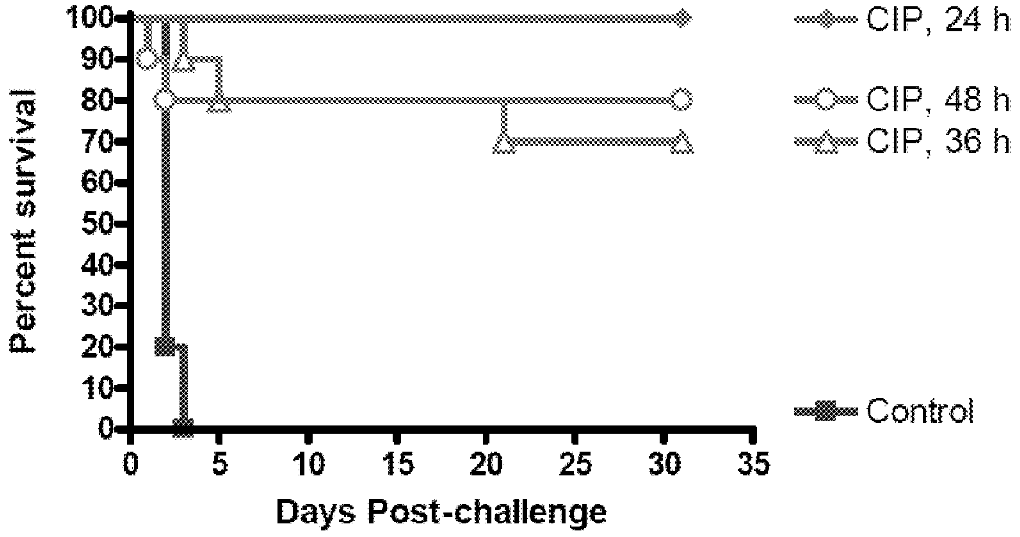
FIG. 5 depicts the proportional survival from ciprofloxacin treatment in the post-exposure treatment model of inhalation anthrax. Control animals received no treatment. Animals in the "CIP" groups received ciprofloxacin at 30 mg/kg q12 h i.p. for 14 days. Treatment was initiated at either 24 h ("CIP, 24 h"), 36 h ("CIP, 36 h") or 48 h ("CIP, 48 h") post-challenge.
Figure 6:
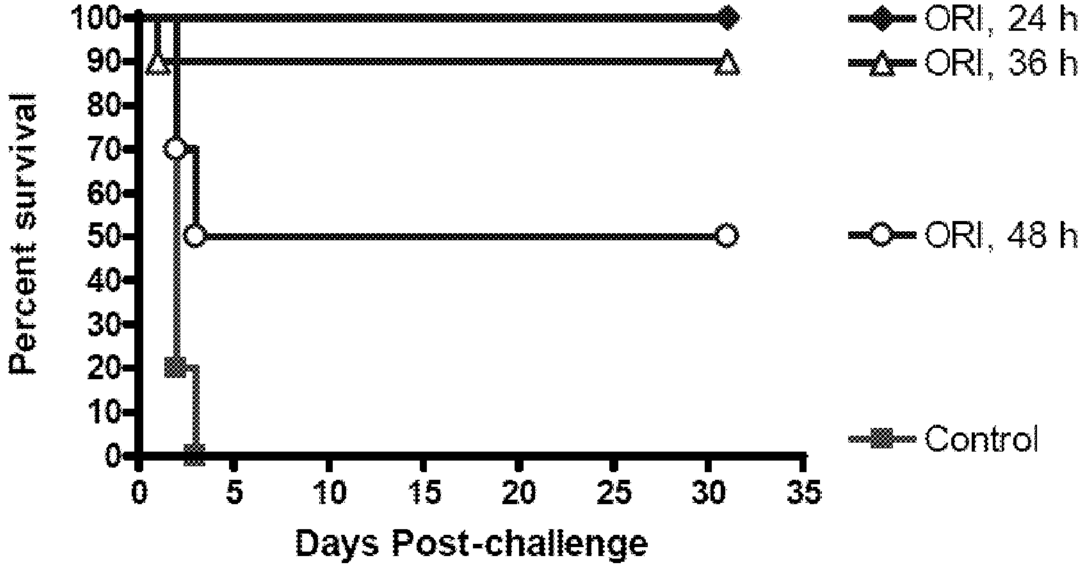
FIG. 6 depicts the proportional survival from oritavancin treatment in the post-exposure treatment model of inhalation anthrax. Control animals received no treatment. Animals in the "ORI" groups received oritavancin at 10 mg/kg q48 h i.p. for 14 days. Treatment was initiated at either 24 h ("ORI, 24 h"), 36 h ("ORI, 36 h") or 48 h ("ORI, 48 h") post-challenge.

Oritavancin (10 mg/kg i.p. q48 h) and ciprofloxacin (30 mg/kg i.p. q12 h) provided equivalent protection when treatment was initiated 36 hours post-challenge (compare FIG. 5, CIP, 36 h to FIG. 6, ORI, 36 h). When treatment was further delayed to 48 h post-challenge, the oritavancin treatment group demonstrated 50% proportional survival relative to 80% in the corresponding ciprofloxacin treatment group (compare FIG. 5, CIP, 48 h to FIG. 6, ORI, 48 h); however, it should be noted that there was no statistical significance to this difference and that all treatment groups had proportional survival rates that were significantly different from the untreated control. Table 2 shows that the spore/tissue load was within the range of $10^3$ to $10^4$ CFU/g tissue, a range that is consistent with survival (Heine et al., 2007, supra).

TABLE 2

Post-treatment Spore Counts in Mouse Lung Tissue from Post-exposure Treatment Model (Delayed Treatment) of Inhalation Anthrax

| Treatment (duration: 14 days) | Initiation of treatment (h post-challenge) | CFU/g tissue[a] |
|---|---|---|
| Ciprofloxacin 30 mg/kg q12 h | 24 | $1.09 \times 10^3$ |
| Ciprofloxacin 30 mg/kg q12 h | 36 | $2.88 \times 10^3$ |
| Ciprofloxacin 30 mg/kg q12 h | 48 | $3.08 \times 10^3$ |
| Oritavancin 10 mg/kg i.p. q48 h | 24 | $3.50 \times 10^3$ |
| Oritavancin 10 mg/kg i.p. q48 h | 36 | $2.52 \times 10^3$ |
| Oritavancin 10 mg/kg i.p. q48 h | 48 | $1.68 \times 10^3$ |

[a]Tissues collected on day 31 postchallenge

Experiment 6

Single Dose Efficacy Study in the Post-exposure Treatment Model

Figure 7:
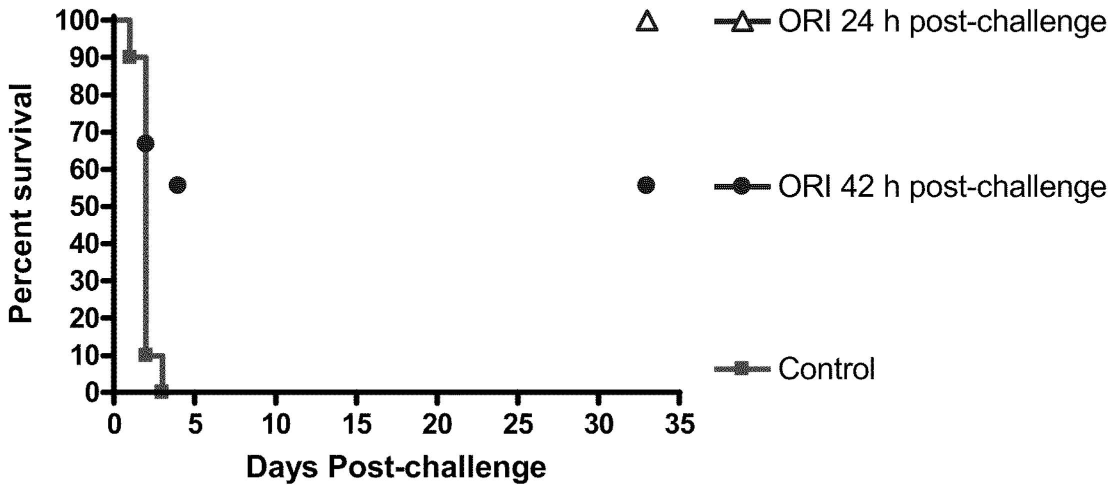
FIG. 7 depicts the proportional survival of mice receiving a single dose of oritavancin (ORI; 50 mg/kg i.v.) 24 or 42 h post-challenge.

To further characterize oritavancin efficacy in post-symptom treatment (Heine et al., 2007, supra), a second study was performed in which therapy with oritavancin was delayed to 42 h post-challenge. Single i.v. doses of 50 mg/kg oritavancin administered 24 h (as efficacy control) and 42 h post-challenge protected 10/10 (100%) and 5/9 (55%) of mice, respectively (FIG. 7). These findings concur with the proportional survival rate that was encountered when the initiation of multiple-dose i.p. oritavancin therapy was delayed to 48 h post-challenge (50%; FIG. 6). It should be noted that the proportional survival that was observed in the post-exposure treatment model of anthrax with i.p. and i.v. oritavancin treatment, whether initiated 36, 42, or 48 h post-exposure, was significantly different from that in the control (untreated) group.

The extended efficacy of oritavancin in vivo, as demonstrated here, predicts that infrequent dosing of oritavancin may be sufficient for protection in humans since oritavancin exhibits a prolonged duration of efficacy. Furthermore, these studies demonstrate that oritavancin, when administered as multiple doses starting at up to 48 h post-challenge, and even when administered as a single dose at 42 h post-challenge, provides a significant level of protection to mice. Oritavancin may therefore have utility in treating subjects that have begun to shown clinical signs of anthrax.

Experiment 7

Single-Dose Efficacy Study in the Pre-Exposure Prophylaxis Model

Based on the results of the post-exposure prophylaxis and the post-exposure treatment studies described above, a follow-up experiment was performed in which a single 50 mg/kg i.v. dose of oritavancin was administered 24 h prior to challenge. Clinical signs and survivorship were evaluated daily until day 31.

Figure 8:
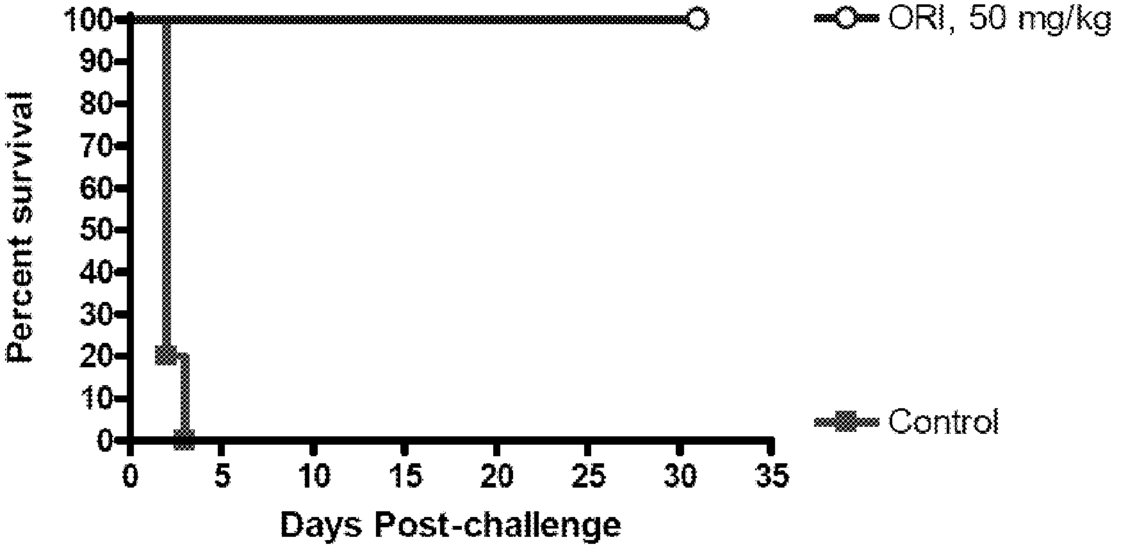
FIG. 8 depicts the proportional survival from oritavancin treatment in the pre-exposure prophylaxis model of inhalation anthrax. Control animals received no treatment. Animals in the "ORI, 50 mg/kg" group received a single 50 mg/kg i.v. dose of oritavancin 24 hours prior to aerosol challenge.

At this dose, oritavancin was found to protect 100% of animals as measured at 31 days post challenge (FIG. 8). Table 3 shows that the spore/tissue load was within the survival range of $10^3$ to $10^4$ CFU/g tissue as was observed in previous experiments (Heine et al., 2007, supra).

TABLE 3

Post-treatment Spore Counts in Mouse Lung Tissue from Pre-exposure Prophylaxis Model of Inhalation Anthrax

| Treatment | Initiation of treatment | CFU/g tissue[a] |
|---|---|---|
| Oritavancin 50 mg/kg i.v. | 24 h pre-challenge | $1.98 \times 10^3$ |

[a]Tissues collected on day 31 postchallenge

Oritavancin efficacy trials were extended to examine the protection afforded by single 50 mg/kg doses of oritavancin given seven days prior to challenge, so as to further characterize the duration of efficacy resulting from a single dose of oritavancin.

Figure 9:
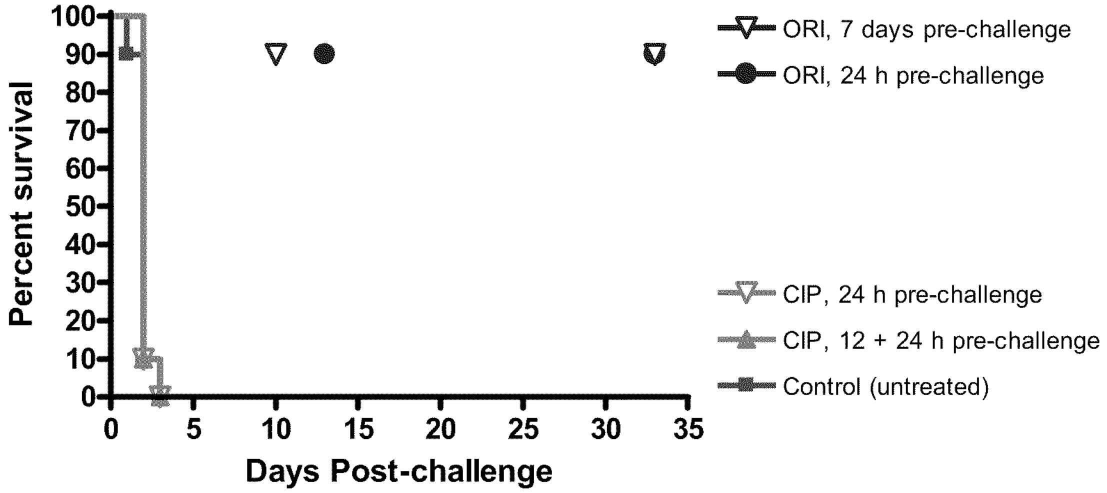
FIG. 9 depicts the proportional survival of mice receiving a single dose of oritavancin (ORI; 50 mg/kg i.v.) or one or two doses of ciprofloxacin (CIP; 30 mg/kg i.p.) prior to spore challenge.

The results demonstrated that oritavancin, when administered in a single i.v. dose of 50 mg/kg either one (as efficacy control) or seven days prior to lethal spore challenge, protected 90% (9/10) of animals at the 33 day post-exposure endpoint (FIG. 9). In contrast, ciprofloxacin, when administered either as a single 30 mg/kg i.p. dose 24 h prior to spore challenge or as two 30 mg/kg i.p. doses, 24 h and 12 h prior to spore challenge, failed to provide any protection since all mice died from infection by day 4 post-challenge (FIG. 9).

Experiment 8

Determination of Bacterial Burden in Tissue

Tissue-bacterial burdens were determined from dead or moribund animals. Surviving mice from each group were euthanized at day 30. Lungs were aseptically removed, weighed and homogenized in 1 mL of sterile water. Homogenates were serially diluted 1:10 in water and 100 µL aliquots were plated on SBAP. To determine if anthrax spores were present, homogenates were "heat shocked" for 15 minutes at 65° C. to kill vegetative cells then serially diluted and plated on SBAP. Antibiotic susceptibilities were determined by the microdilution method as described above. The results are shown in Table 4.

TABLE 4

Summary of Efficacy and Post-treatment Spore Counts in Mouse Lung Tissue.

| Agent | Regimen | Start of therapy (h post challenge) | Proportional survival at 30/31 d (%; n = 10) | Spore load in lung (CFU/g) |
|---|---|---|---|---|
| None | — | — | 0* | n.d. |
| CIP | 30 mg/kg q12 h × 14 d | 24 h | 90 | $5.20 \times 10^4$ |
| ORI | 30 mg/kg i.p. q48 h × 14 d | 24 h | 100 | $1.82 \times 10^4$ |
| | 10 mg/kg i.p. q48 h × 14 d | 24 h | 100 | $4.79 \times 10^4$ |
| | 3 mg/kg i.p. q48 h × 14 d | 24 h | 100 | $3.68 \times 10^4$ |
| | 1 mg/kg i.p. q48 h × 14 d | 24 h | 50 | $2.95 \times 10^4$ |
| | 0.3 mg/kg i.p. q48 h × 14 d | 24 h | 30 | $2.80 \times 10^4$ |
| | 50 mg/kg i.v. single dose | 24 h | 100 | $3.61 \times 10^4$ |
| | 15 mg/kg i.v. single dose | 24 h | 70 | $2.03 \times 10^4$ |
| | 5 mg/kg i.v. single dose | 24 h | 40 | $3.50 \times 10^4$ |
| CIP | 30 mg/kg q12 h × 14 d | 24 h | 100 | $1.09 \times 10^3$ |
| | | 36 h | 70 | $2.88 \times 10^3$ |
| | | 48 h | 80 | $3.08 \times 10^3$ |
| ORI | 10 mg/kg i.p. q48 h × 14 d | 24 h | 100 | $3.50 \times 10^3$ |
| | | 36 h | 90 | $2.52 \times 10^3$ |
| | | 48 h | 50 | $1.68 \times 10^3$ |
| ORI | 50 mg/kg i.v. single dose | −24 h | 100 | $1.98 \times 10^3$ |

*100% dead at 4 d

Experiments 3 to 7

Summary

Oritavancin is active in a mouse model of post-exposure prophylaxis of inhalation anthrax: oritavancin administered by either the i.p. route or i.v. route increased the proportional survival of mice that had received a lethal challenge of *B. anthracis* spores. Oritavancin administered i.p. at 3 mg/kg once every other day for 14 days or i.v. at 50 mg/kg as a single dose was at least as active, respectively, as ciprofloxacin at 30 mg/kg administered twice daily for 14 days. An oritavancin dosing regimen is thus is more convenient than the positive control ciprofloxacin treatment regimen since a single i.v. dose or seven i.p. doses of oritavancin at the proper dose level achieved the same proportional survival as did 28 doses of ciprofloxacin.

Delay of treatment to 36 and 48 hours has been demonstrated to induce development of symptoms and bacteremia in the mouse aerosol anthrax model (Heine et al., 2007, supra). Oritavancin demonstrated potent activity in this model of post-exposure treatment when administered q48 h i.p. for 14 days, achieving 90% and 50% protection following 10 mg/kg dosing when treatment was initiated at 36 and 48 h post-challenge, respectively. Furthermore, delay of single-dose oritavancin treatment to 42 h post-challenge also yielded significant (55%) protection.

The pre-exposure prophylaxis that was afforded by a single 50 mg/kg i.v. dose of oritavancin both 24 hours and 7 days prior to aerosol challenge further highlights the extended half-life of oritavancin. Furthermore, this finding suggests that oritavancin may concentrate in those cellular compartments where spores may be germinating in the early stages of the infection. This idea is consistent with literature data that show significant intracellular accumulation of oritavancin in macrophages in vitro (Van Bambeke et al. 2004. *Antimicrob. Agents Chemother.* 48:2853-2860).

The in vitro susceptibility data and in vivo efficacy data described here suggest that oritavancin could serve as a therapy for pre-exposure prophylaxis, post-exposure prophylaxis, and post-exposure treatment of inhalation anthrax. Due to the persistence of spores in the lungs and tissues of individuals exposed to *B. anthracis*, currently approved therapies must continue for 60 days. The enhanced efficacy of oritavancin in vivo in the mouse aerosol model suggests that less frequent dosing (including single-dose dosing) of oritavancin relative to ciprofloxacin may still provide a similar degree of protection. In addition, multiple mechanisms of action for oritavancin (Allen and Nicas, 2003. FEMS Microbiol. Rev. 26: 511-532; McKay et al. 2006. *Poster C*1-682. 46th annual Interscience Conference on Antimicrobial Agents and Chemotherapy (ICAAC), San Francisco, Calif., Sep. 27-30, 2006) may allow it to retain activity against drug-resistant strains of *B. anthracis*, including those resistant to vancomycin, to other cell-wall active antibiotics, and to other classes of antibiotics.

The invention has been described herein both generically and with regard to specific embodiments. Although the invention has been set forth in what is believed to be the preferred embodiments, a wide variety of alternatives known to those of skill in the art can be selected within the generic disclosure. The invention is not otherwise limited, except for in the recitation of the claims.

All documents, publications, patents, books, manuals, articles, papers, abstracts, posters and other materials referenced herein are expressly incorporated herein by reference in their entireties.

We claim:

1. A method of preventing a *B. anthracis* infection in a subject, consisting of administering to a subject at risk of exposure to *B. anthracis* one or more antibiotics in an amount sufficient to prevent *B. anthracis* infection, wherein the one or more antibiotics includes oritavancin, or a pharmaceutically acceptable salt, or hydrate thereof, or a mixture thereof, thereby preventing a *B. anthracis* infection in a subject.

2. The method of claim 1 wherein the one or more antibiotics are administered less than about 24 hours prior to the risk of exposure.

3. The method of claim 1 wherein the one or more antibiotics are administered less than about 15 days prior to the risk of exposure.

4. The method of claim 1 wherein the duration of the prevention is at least 30 days.

5. The method of claim 1 wherein the administration to the subject of the one or more antibiotics is a single dose of each of the antibiotics.

6. The method of claim 1 wherein the administration to the subject of the one or more antibiotics is a dose of each of the antibiotics once every 48 hours.

7. The method of claim 1 wherein the administration to the subject of the one or more antibiotics is a dose of each of the antibiotics once weekly.

8. The method of claim 1 wherein the administration of the antibiotics is independently by intravenous administration or intraperitoneal administration.

9. The method of claim 1 wherein *B. anthracis* is a vegetative form of *B. anthracis*, a *B. anthracis* spore or a mixture of both.

10. The method of claim 1 wherein the *B. anthracis* infection is selected from the group consisting of cutaneous anthrax, gastrointestinal anthrax or inhalational anthrax.

11. The method of claim 1 wherein the one or more antibiotics are in the form of one or more pharmaceutical compositions comprising the antibiotics and a pharmaceutically acceptable carrier or diluent.

12. The method of claim 1 wherein the one or more antibiotics is oritavancin, or a pharmaceutically acceptable salt, or hydrate thereof, or a mixture thereof.

13. The method of claim 1 wherein the one or more antibiotics are oritavancin and one antibiotic compound selected from the group consisting of a glycopeptide, a fluoroquinolone, a tetracycline, a macrolide, a β-lactam, an ansamycin, a phenicol, a streptogramin, an aminoglycoside, an oxazolidinone, a tetracycline, a glycylglycine, a cyclic lipopeptide and a lincosamine, or pharmaceutically acceptable salts, or hydrates thereof, or mixtures thereof.

14. The method of claim 1 wherein the one or more antibiotics are oritavancin and one antibiotic compound selected from the group consisting of vancomycin, ciprofloxacin, doxycycline, erythromycin, cethromycin, azithromycin, clarithromycin, penicillin, imipenem, ampicillin, rifampin, chloramphenicol, quinupristin-dalfopristin, gentamicin, linezolid, tetracycline, tigecycline, daptomycin and clindamycin.

15. The method of claim 1 wherein the one or more antibiotics are oritavancin and two antibiotic compounds selected from the group consisting of a glycopeptide, a fluoroquinolone, a tetracycline, a macrolide, a β-lactam, an ansamycin, a phenicol, a streptogramin, an aminoglycoside, an oxazolidinone, a tetracycline, a glycylglycine, a cyclic lipopeptide and a lincosamine, or pharmaceutically acceptable salts, or hydrates thereof, or mixtures thereof.

16. The method of claim 1 wherein the one or more antibiotics are oritavancin and two antibiotic compounds selected from the group consisting of vancomycin, ciprofloxacin, doxycycline, erythromycin, cethromycin, azithromycin, clarithromycin, penicillin, imipenem, ampicillin, rifampin, chloramphenicol, quinupristin-dalfopristin, gentamicin, linezolid, tetracycline, tigecycline, daptomycin and clindamycin.

* * * * *